(12) United States Patent
Schon et al.

(10) Patent No.: US 8,206,354 B2
(45) Date of Patent: Jun. 26, 2012

(54) METHOD FOR INSERTING A CATHETER

(75) Inventors: Donald A. Schon, Paradise Valley, AZ (US); Timothy Schweikert, Levittown, PA (US); Kevin Sanford, Chalfont, PA (US); John Stephens, Perkiomenville, PA (US); Earl Voorhees, Jr., Warrington, PA (US); Mahase Nardeo, Collegeville, PA (US)

(73) Assignees: Medical Components, Inc., Harleysville, PA (US); TwinCath LLC, Paradise Valley, AZ (US)

( * ) Notice: Subject to any disclaimer, the term of this patent is extended or adjusted under 35 U.S.C. 154(b) by 0 days.

(21) Appl. No.: 12/535,341

(22) Filed: Aug. 4, 2009

(65) Prior Publication Data
US 2009/0292248 A1 Nov. 26, 2009

Related U.S. Application Data

(62) Division of application No. 10/974,267, filed on Oct. 27, 2004, now Pat. No. 7,918,817.

(51) Int. Cl.
*A61M 25/01* (2006.01)
(52) U.S. Cl. ........ 604/164.01; 604/27; 604/43; 604/171
(58) Field of Classification Search .................. 604/43, 604/513, 523, 533–535, 537–539, 284, 264, 604/913, 500, 506–508, 104, 93.01, 158, 604/164.01, 164.03, 164.04, 164.09–164.11, 604/170.01, 170.02, 174, 175, 271, 544, 604/28, 27, 171
See application file for complete search history.

(56) References Cited

U.S. PATENT DOCUMENTS

| | | | |
|---|---|---|---|
| 3,957,082 A | 5/1976 | Fuson et al. |
| 4,037,599 A | 7/1977 | Raulerson |
| 4,149,539 A | 4/1979 | Cianci |
| 4,405,313 A | 9/1983 | Sisley et al. |
| 4,568,329 A | 2/1986 | Mahurkar |

(Continued)

FOREIGN PATENT DOCUMENTS

EP 0385168 A2 5/1990

(Continued)

OTHER PUBLICATIONS

Trial Decision, JP Application. 2000-506899 Feb. 02, 2009 (8 pages) Translation (15 pages).

(Continued)

*Primary Examiner* — Quynh-Nhu H Vu
(74) *Attorney, Agent, or Firm* — Peter K. Zacharias; Blank Rome LLP

(57) ABSTRACT

A method for inserting a multiple catheter assembly into a patient. The assembly includes a first catheter which includes a first distal end region, a first outer surface defining a first lumen, and a first transition region transitioning cross sections of the first outer surface and the first lumen. A second catheter includes a second distal end region, a second outer surface defining a second lumen, and a second transition region transitioning cross sections of the second outer surface and the second lumen. The outer surfaces of the first and second catheters are releasably joined by a splittable bond for allowing first and second distal tips of the assembly to be at least partially longitudinally split from each other. The method includes steps of separating the first and second distal end regions, and inserting the first and second distal tips through an incision and into an area to be catheterized.

19 Claims, 16 Drawing Sheets

U.S. PATENT DOCUMENTS

| | | | |
|---|---|---|---|
| 4,682,978 A | 7/1987 | Martin | |
| 4,895,561 A | 1/1990 | Mahurkar | |
| 4,925,452 A | 5/1990 | Melinyshyn et al. | |
| 4,995,387 A | 2/1991 | Jinotti | |
| 5,037,405 A | 8/1991 | Crosby | |
| 5,053,023 A | 10/1991 | Martin | |
| 5,059,170 A | 10/1991 | Cameron | |
| 5,324,253 A | 6/1994 | McRea et al. | |
| 5,575,767 A | 11/1996 | Stevens | |
| 5,599,328 A | 2/1997 | Stevens | |
| 5,624,413 A * | 4/1997 | Markel et al. | 604/523 |
| 5,718,692 A | 2/1998 | Schon et al. | |
| 5,776,111 A | 7/1998 | Tesio | |
| 5,800,414 A | 9/1998 | Cazal | |
| 5,807,311 A | 9/1998 | Palestrant | |
| 5,947,953 A * | 9/1999 | Ash et al. | 604/508 |
| 6,001,079 A | 12/1999 | Pourchez | |
| 6,156,016 A | 12/2000 | Maginot | |
| 6,190,349 B1 * | 2/2001 | Ash et al. | 604/43 |
| 6,248,092 B1 | 6/2001 | Miraki et al. | |
| 6,361,523 B1 | 3/2002 | Bierman | |
| 6,497,681 B1 | 12/2002 | Brenner | |
| 6,582,403 B1 | 6/2003 | Bierman et al. | |
| 6,663,600 B2 | 12/2003 | Bierman et al. | |
| 6,689,096 B1 | 2/2004 | Loubens | |
| 6,695,832 B2 | 2/2004 | Schon et al. | |
| 6,719,727 B2 | 4/2004 | Brimhall et al. | |
| 6,719,749 B1 | 4/2004 | Schweikert et al. | |
| 6,758,836 B2 | 7/2004 | Zawacki | |
| 6,758,854 B1 | 7/2004 | Butler et al. | |
| 6,872,198 B1 * | 3/2005 | Wilson et al. | 604/513 |
| 6,881,211 B2 * | 4/2005 | Schweikert et al. | 604/544 |
| 6,921,396 B1 * | 7/2005 | Wilson et al. | 604/508 |
| 6,951,550 B2 * | 10/2005 | Bierman | 604/174 |
| 6,969,381 B2 | 11/2005 | Voorhees | |
| 6,991,625 B1 * | 1/2006 | Gately et al. | 604/523 |
| 7,347,852 B2 | 3/2008 | Hobbs et al. | |
| 7,393,339 B2 * | 7/2008 | Zawacki et al. | 604/43 |
| 2002/0099326 A1 | 7/2002 | Wilson et al. | |
| 2002/0099327 A1 | 7/2002 | Wilson et al. | |
| 2002/0107475 A1 | 8/2002 | Maginot | |
| 2002/0120224 A1 | 8/2002 | Zia et al. | |
| 2003/0088213 A1 | 5/2003 | Schweikert et al. | |
| 2003/0097091 A1 | 5/2003 | Hobbs et al. | |
| 2003/0153898 A1 | 8/2003 | Schon et al. | |
| 2004/0092863 A1 * | 5/2004 | Raulerson et al. | 604/43 |
| 2005/0096585 A1 * | 5/2005 | Schon et al. | 604/43 |

FOREIGN PATENT DOCUMENTS

| | | |
|---|---|---|
| EP | 0836863 A1 | 4/1998 |
| JP | 64-952 | 1/1989 |
| JP | 2001-137350 | 5/2001 |
| JP | 2001-513357 | 9/2001 |
| JP | 2001-340466 | 12/2001 |
| WO | WO99/07301 | 2/1999 |
| WO | WO03/033049 | 4/2003 |
| WO | WO03/066148 | 8/2003 |

OTHER PUBLICATIONS

Court Hearing in Writing, JP2000-506899 dated Jul. 15, 2008 (2 pages).
In'tl Search Report, PCT/US04/35580 dated Aug. 31, 2006 (4 pages).
Written Opinion of In'tl Searching Authority, PCT/US04/35580 dated Aug. 31, 2006 (3 pages).
Supplemental European Search Report, EP Application No. 04796500.9-2310 dated Aug. 21, 2007 (3 pages).
CA Application 2,543,929 Office Action, dated Jan. 7, 2010, 2 pages.
CA Application 2,543,929 Office Action, dated Sep. 9, 2008, 2 pages.
CA Application 2,543,929 Response to Office Action, filed Jul. 7, 2010, 13 pages.
CA Application 2,543,929 Response to Office Action, filed Mar. 9, 2009, 9 pages.
EP Application 04796500.9 Communication, dated Aug. 13, 2010, 55 pages.
EP Application 04796500.9 Communication, dated Aug. 21, 2007, 5 pages.
EP Application 04796500.9 Communication, dated Jul. 29, 2010, 2 pages.
EP Application 04796500.9 Communication, dated Nov. 12, 2009, 3 pages.
EP Application 04796500.9 Preliminary Amendment, dated Nov. 12, 2007, 5 pages.
EP Application 04796500.9 Response, dated Jul. 29, 2010, 3 pages.
EP Application 04796500.9 Response, dated Mar. 11, 2010, 9 pages.
EP Application No. 03777942.8 Search Report, dated Apr. 7, 2006, 3 pages.
JP Application 2006-538203 Office Action, dated Apr. 6, 2010, 2 pages, with translation (3 pages).
JP Application 2006-538203 Office Action, dated Aug. 11, 2009, 2 pages, with translation (3 pages).
U.S. Appl. No. 10/974,267 Office Action, dated Jun. 11, 2008, (6 pages).
U.S. Appl. No. 10/974,267 Office Action, dated May 18, 2009, (9 pages).
U.S. Appl. No. 10/974,267 Office Action, dated May 24, 2010, (7 pages).
U.S. Appl. No. 10/974,267 Interview Summary, Nov. 30, 2010 (1 page).
U.S. Appl. No. 10/974,267 Office Action, dated Dec. 30, 2008, (9 pages).
U.S. Appl. No. 10/974,267 Office Action, dated Nov. 1, 2006, (7 pages).
U.S. Appl. No. 10/974,267 Office Action, dated Oct. 15, 2009, (11 pages).
U.S. Appl. No. 10/974,267 Office Action, dated Sep. 6, 2006, (6 pages).
U.S. Appl. No. 10/974,267 Response to Office Action, dated Feb. 16, 2010 (18 pages).
U.S. Appl. No. 10/974,267 Response to Office Action, dated Jul. 27, 2009 (17 pages).
U.S. Appl. No. 10/974,267 Response to Office Action, dated Mar. 23, 2009 (26 pages).
U.S. Appl. No. 10/974,267 Response to Office Action, dated Oct. 25, 2010 (18 pages).
U.S. Appl. No. 10/974,267 Response to Office Action, dated Sep. 11, 2008 (19 pages).
U.S. Appl. No. 10/974,267 Response to Office Action, dated Jan. 31, 2007, (22 pages).
U.S. Appl. No. 10/974,267 Response to Office Action, dated Oct. 6, 2006, (2 pages).
EP Application 10015357.6 Search Report, dated Feb. 24, 2011, 6 pages.
U.S. Appl. No. 10/974,267 Notice of Allowance, dated Jan. 21, 2011, 12 pages.
CA Application 2,543,929 Notice of Allowance, dated Feb. 2, 2011, 1 page.
CA Application 2,660,712 Office Action, dated Sep. 9, 2010, 2 pages.
CA Application 2,660,712 Response, dated Mar. 3, 2011, 14 pages.
CA Application 2,660,712 Notice of Allowance, dated Apr. 7, 2011, 2 pages.

* cited by examiner

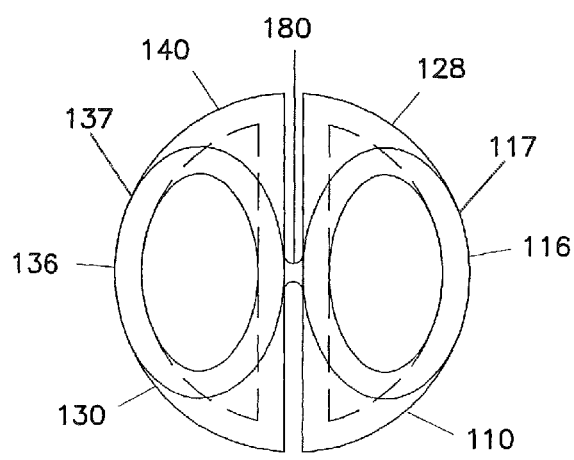
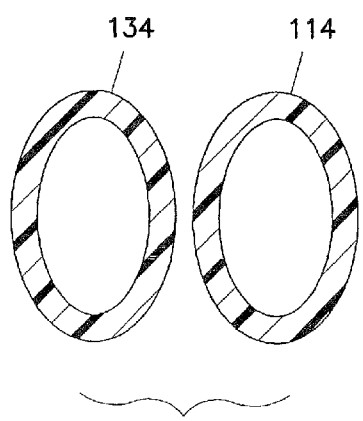
FIG. 4
FIG. 3
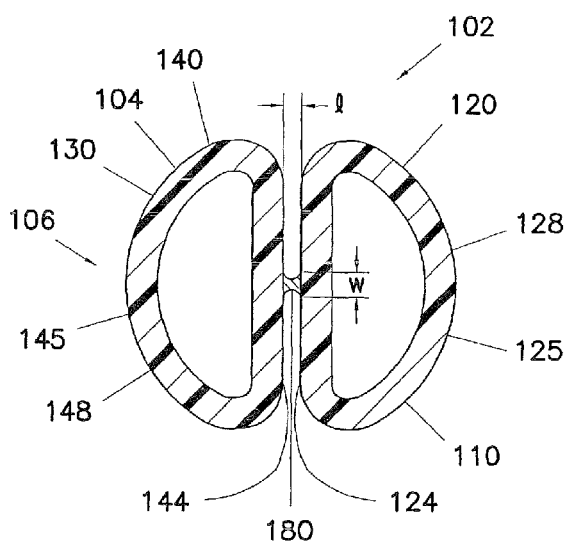
FIG. 2

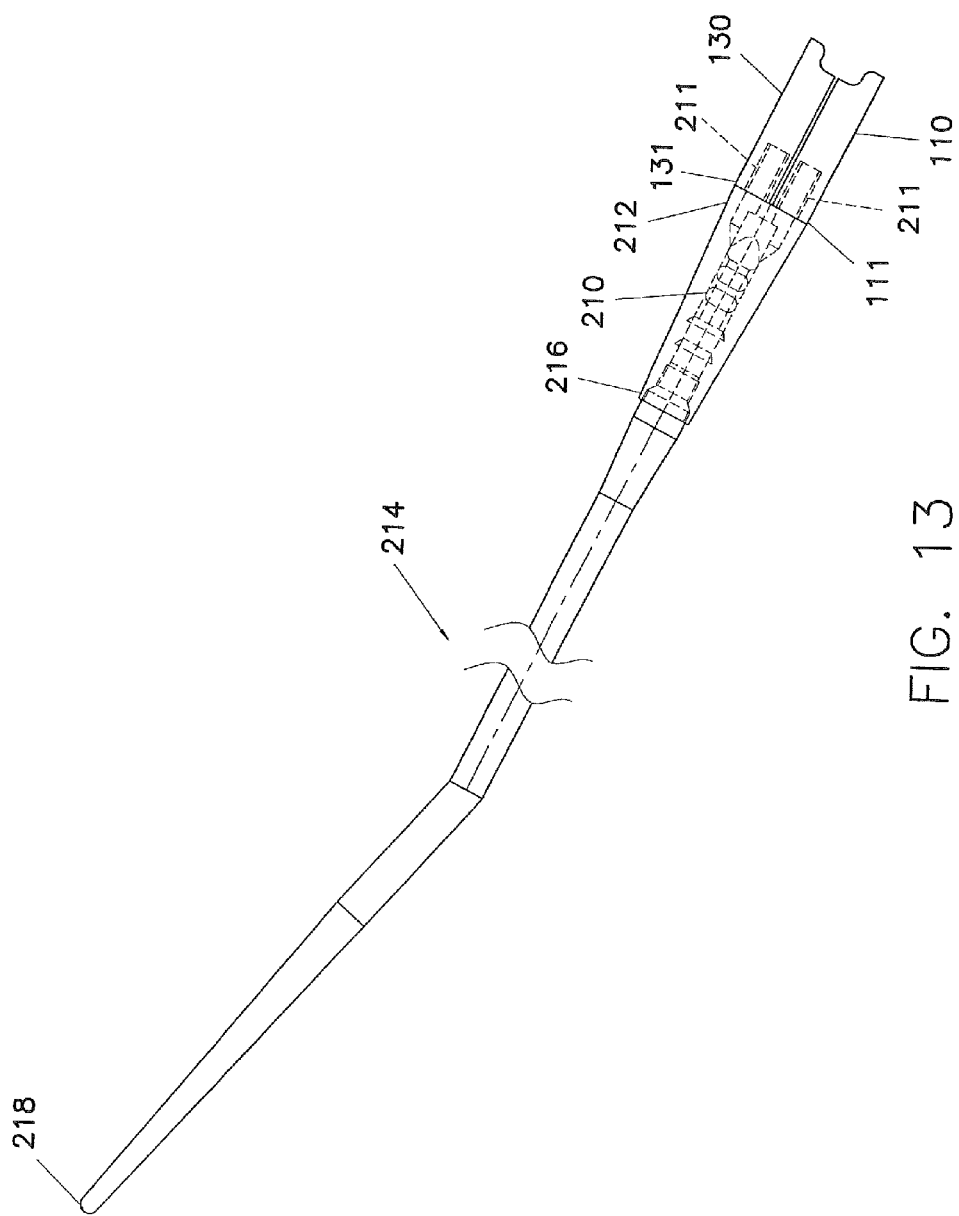

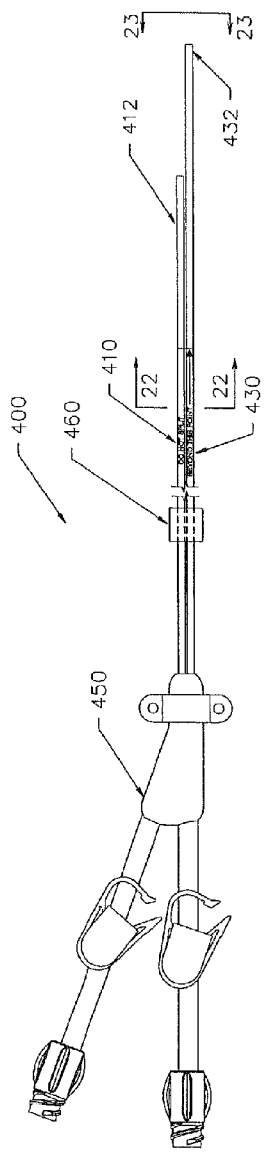
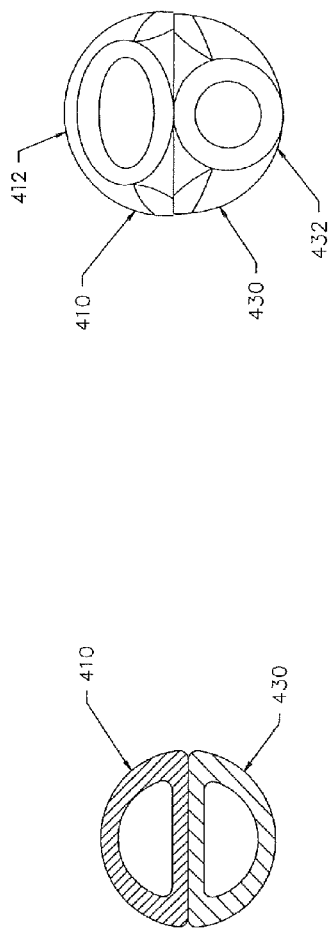
FIG. 21
FIG. 23
FIG. 22

METHOD FOR INSERTING A CATHETER

CROSS-REFERENCE TO RELATED APPLICATIONS

The present application is a Divisional of U.S. patent application Ser. No. 10/947,267, filed Oct. 24, 2004, which is a Continuation-in-Part of U.S. patent application Ser. No. 10/695,178, filed Oct. 28, 2003, which claims the benefit of U.S. Provisional Patent Application Ser. No. 60/422,726, filed Oct. 31, 2002 and U.S. Provisional Patent Application Ser. No. 60/423,002, filed Nov. 1, 2002.

FIELD OF THE INVENTION

The present invention relates to splittable multiple catheter assemblies, typically used for hemodialysis.

BACKGROUND OF THE INVENTION

Catheters for the introduction or removal of fluids may be located in various venous locations and cavities throughout the body for introduction or removal of these fluids. Such catheterization may be performed by using a single catheter having multiple lumens. A typical example of a multiple lumen catheter is a dual lumen catheter assembly in which one lumen introduces fluid and the other lumen removes fluid. An example of such a dual lumen catheter assembly is the SPLIT CATH® catheter, manufactured and sold by Medical Components, Inc. of Harleysville, Pa.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the guide wire within the vessel. The guide wire projects beyond the surface of the skin. At this point, several options are available to a surgeon for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire, for example, for insertion of small diameter dual lumen catheters. If the catheter to be inserted is significantly larger than the guide wire, a dilator device is passed over the guide wire to enlarge the hole. The dilator is removed and the catheter is then passed over the guide wire. After the catheter is inserted, the guide wire is removed.

For chronic catheterization, in which the catheter is intended to remain inside the patient for extended period of time, such as for weeks or even months, it is typically desired to subcutaneously tunnel the catheter using various tunneling techniques. The catheter is typically tunneled into the patient prior to inserting the catheter into the patient's vein. At some point after tunneling, the catheter hub is sutured onto the patient's skin to secure the proximal end of the catheter to the patient.

However, there may be times when it is more advantageous, such as depending on the patient or the implanting surgeon's skill, to perform the tunneling after the catheter is implanted in the patient. For some catheters, though, such as multiple lumen catheters with a hub and with bonded luers on the proximal ends of the catheters, it is impractical to perform the tunneling after the catheter is installed in the patient. It would be beneficial to provide a catheter assembly that provides a surgeon with alternative installation procedures for installing the catheter that better suit either the patient's needs or the surgeon's skills.

Further, for chronically installed catheters, portions of the catheter external to the patient occasionally fail, such as for instance, by leaking and/or by the introduction of foreign particles such as dirt, bacteria, and the like into the catheter, necessitating removal of the entire catheter from the patient. Such failures include worn or broken clamps or broken luers. In order to correct these problems, it is presently necessary to remove the entire catheter from the patient, causing additional trauma to the patient and risking additional medical problems to the patient. It would be beneficial to provide a catheter in which the proximal portion of the catheter may be removed and replaced without disturbing the distal portion of the catheter inside the patient.

Also, while catheter assemblies typically are manufactured in standard sizes, such as 12 French, 14 French, etc., patients come in many various shapes and sizes. Where a particular size catheter may be an optimum size for one patient, the surgeon may desire or require a different length of a subcutaneous tunnel for a different patient. However, the location of the catheter hub may dictate the length and/or location of the subcutaneous tunnel. It would be beneficial to provide a catheter assembly that has an adjustable location for the hub along the catheter assembly to provide the surgeon options for securing the catheter assembly to the patient.

BRIEF SUMMARY OF THE INVENTION

Briefly, the present invention provides a multiple catheter assembly. The assembly includes a first catheter constructed from a first material and having a first proximal end region, a first distal end region terminating in a first distal tip, and an outer surface defining at least a first lumen extending longitudinally therethrough between a first distal and a first proximal opening. The first proximal end region is integrally connected to an extension tube constructed from a second material. A second catheter is constructed from the first material and having a second proximal end region, a second distal end region terminating in a second distal tip, and a second outer surface defining at least a second lumen extending longitudinally therethrough between a second distal and a second proximal opening. The second proximal end region is integrally connected to an extension tube constructed from the second material. The first and second lumens are independent from each other for facilitating simultaneous flow in opposite directions. The outer surfaces of the first and second catheters are releasably joined for allowing the first and second distal tips to be at least partially longitudinally split from each other.

Further, the present invention also provides a method for inserting a multiple catheter assembly into an area of a body to be catheterized. The method comprises: making an incision near the area to be catheterized; and providing a multiple catheter assembly comprising a first catheter constructed from a first material and having a first proximal end region, a first distal end region terminating in a first distal tip, and an outer surface defining at least a first lumen extending longitudinally therethrough between a first distal and a first proximal opening. The first proximal end region is integrally connected to an extension tube constructed from a second material. The catheter also comprises a second catheter constructed from the first material and having a second proximal end region, a second distal end region terminating in a second distal tip, and a second outer surface defining at least a second lumen extending longitudinally therethrough between a second distal and a second proximal opening. The second proximal end region is integrally connected to an extension tube constructed from the second material. The first lumen and the second lumens are independent from each other for facilitating simultaneous flow in opposite directions. The outer surfaces of the first and second catheters are releasably joined for allowing the first and second distal tips to be at least partially longitudinally split from each other. The method further comprises at least partially separating the first and second distal end regions of the first and second catheters from each other; and inserting the first and second distal end regions of the first and second catheters in juxtaposed relation to each other through the incision and into the area to be catheterized.

Additionally, the present invention also provides a multiple catheter assembly, comprising a first catheter constructed from a first material and has a first proximal end region, a first distal end region terminating in a first distal tip, and an outer surface defining at least a first lumen extending longitudinally therethrough between a first distal and a first proximal opening. The first lumen has a first cross-sectional shape and the first distal opening has a second cross-sectional shape. A first extension tube is integrally connected to the first proximal end region, wherein the first extension tube is constructed from a second material. A first connector is releasably connected to a proximal end of the first extension tube. A second catheter is constructed from the first material and has a second proximal end region, a second distal end region terminating in a second distal tip, and a second outer surface defining at least a second lumen extending longitudinally therethrough between a second distal and a second proximal opening. The second lumen has the first cross-sectional shape and the second distal opening has a third cross-sectional shape. The second catheter is bonded to the first catheter along a length. A second extension tube is integrally connected to the second proximal end region, wherein the second extension tube is constructed from the second material. A second connector is releasably connected to a proximal end of the second extension tube. A fabric cuff is attachable to the first and second catheters at a position along the length. The first and second lumens are independent from each other for facilitating simultaneous flow in opposite directions.

Additionally, the present invention provides a multiple catheter assembly, comprising a first catheter constructed from a first material and having a first proximal end region, a first distal end region terminating in a first distal tip, and an outer surface defining at least a first lumen extending longitudinally therethrough between a first distal and a first proximal opening. The first lumen has a first cross-sectional shape and the first distal opening has a second cross-sectional shape. A first extension tube is fixedly connected to the first proximal end region, wherein the first extension tube is constructed from a second material. A first connector is connected to a proximal end of the first extension tube. A second catheter is constructed from the first material and has a second proximal end region, a second distal end region terminating in a second distal tip, and a second outer surface defining at least a second lumen extending longitudinally therethrough between a second distal and a second proximal opening. The second lumen has the first cross-sectional shape and the second distal opening has a third cross-sectional shape. The second catheter is bonded to the first catheter along a length. A second extension tube is fixedly connected to the second proximal end region, wherein the second extension tube is constructed from the second material. A second connector is connected to a proximal end of the second extension tube. A fabric cuff is attachable to the first and second catheters at a position along the length. The first and second lumens are independent from each other for facilitating simultaneous flow in opposite directions.

Additionally, the present invention provides a multiple catheter assembly, comprising a first catheter constructed from a first material and having a first proximal end region, a first distal end region terminating in a first distal tip, and an outer surface defining at least a first lumen extending longitudinally therethrough between a first distal and a first proximal opening. The first lumen has a first cross-sectional shape and the first distal opening has a second cross-sectional shape. The catheter assembly also includes a second catheter constructed from the first material and having a second proximal end region, a second distal end region terminating in a second distal tip, and a second outer surface defining at least a second lumen extending longitudinally therethrough between a second distal and a second proximal opening. The second lumen has the first cross-sectional shape and the second distal opening has a third cross-sectional shape. The second catheter is bonded to the first catheter along a length. The first and second lumens are independent from each other for facilitating simultaneous flow in opposite directions. The first and second distal end regions are releasably joined for allowing the first and second distal end regions to be at least partially longitudinally split from each other.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 2 is an enlarged sectional view of the catheter lumens of the catheter assembly taken along lines 2-2 of FIG. 1.

FIG. 3 is an enlarged sectional view of the distal end of the catheter lumens of the catheter assembly taken along lines 3-3 of FIG. 1.

FIG. 4 is an enlarged end view of the distal end of the catheter lumens of the catheter assembly taken along lines 4 of FIG. 1.

FIG. 13 is a perspective view of a catheter tunneler used to pull the proximate end of the catheters through the subcutaneous tunnel.

FIG. 21 is a side elevational view of an alternative embodiment of a catheter assembly according to the present invention.

FIG. 22 is a sectional view of the catheters of the catheter assembly taken along lines 22-22 of FIG. 21.

FIG. 23 is an end view of the catheters of the catheter assembly taken along lines 23-23 of FIG. 21.

DETAILED DESCRIPTION OF THE INVENTION

Figure 1:
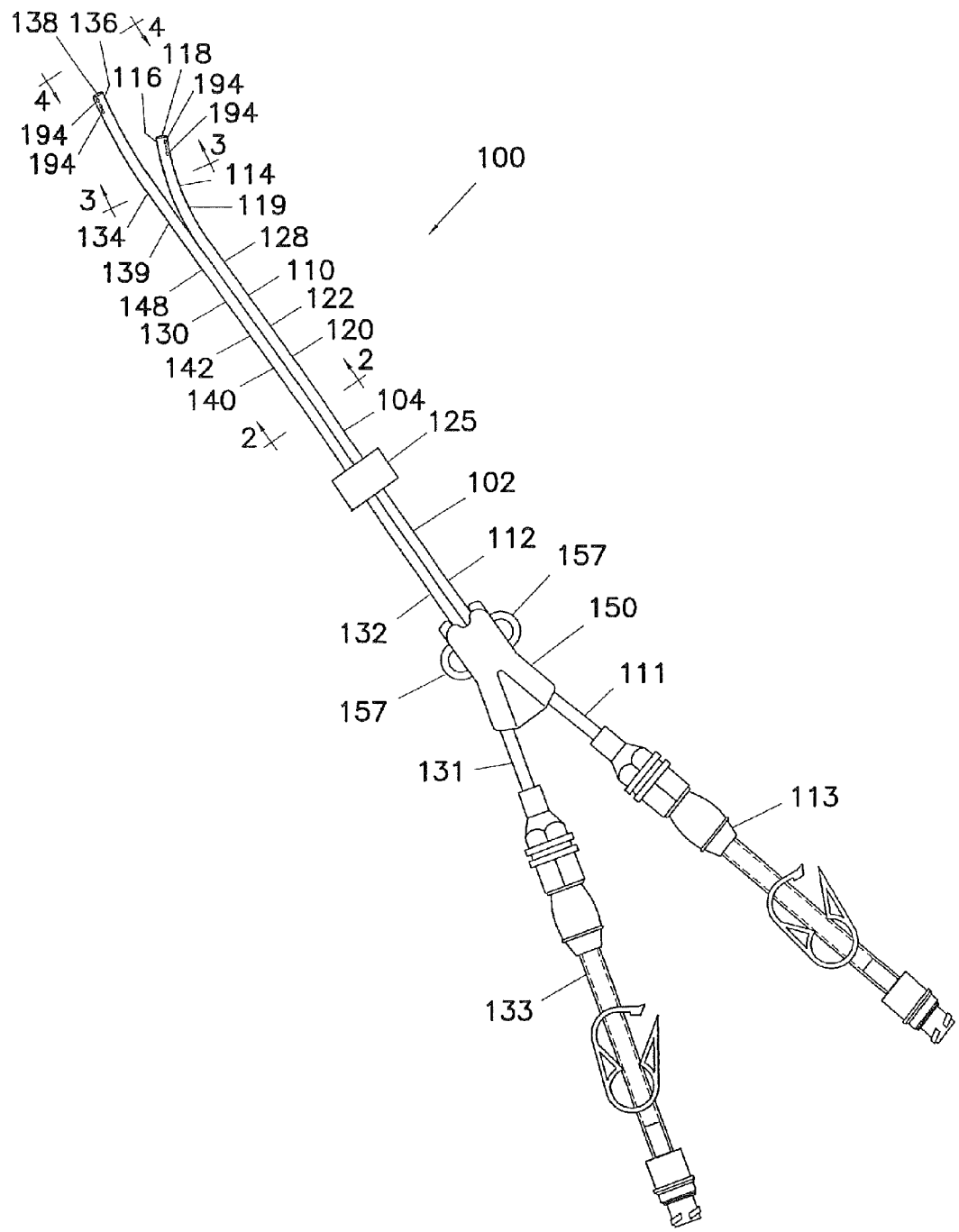
FIG. 1 is a top plan view of a catheter assembly according to a first preferred embodiment of the present invention.

In the drawings, like numerals indicate like elements throughout. Certain terminology is used herein for convenience only and is not to be taken as a limitation on the present invention. The terms "distal" and "proximal" refer, respectively, to the directions "away from" and "closer to" the surgeon inserting the catheter into a patient. The terminology includes the words above specifically mentioned, derivatives thereof, and words of similar import.

The following describes preferred embodiments of the invention. However, it should be understood, based on this disclosure, that the invention is not limited by the preferred embodiments described herein. Referring now to the drawings in detail, there is shown in FIG. 1, an embodiment of a multiple catheter assembly generally indicated as 100. The multiple catheter assembly 100 shown in FIG. 1 is a double catheter assembly, although assemblies having two or more catheters are within the scope of this invention.

The invention as shown in this disclosure is preferably useful for the removal of blood for purification from a blood vessel, such as the internal jugular vein, and introduction of purified blood into the same vessel. However, it will be known to those skilled in the art that the multiple catheter assembly 100 may be used to introduce or remove various fluids in various areas to be catheterized.

The multiple catheter assembly 100 includes a cannulating portion 102 defined by an outer surface 104. The multiple catheter assembly 100 further includes a first catheter 110 at least partially releasably joined to a second catheter 130. The first catheter 110 includes a first proximal end region 112, and a first distal end region 114 having a first distal tip 116. The first distal tip 116 has a first distal opening 118. The first catheter 110 also has a first outer surface 120 defining a first lumen 122. The first lumen 122 fluidly communicates with the first distal opening 118. The second catheter 130 includes a second proximal end region 132, and a second distal end region 134 having a second distal tip 136. The second distal tip 136 has a second distal opening 138. The second catheter 130 also has a second outer surface 140 defining a second lumen 142. The second lumen 142 fluidly communicates with the second distal opening 138. Preferably, the first distal tip 116 ends approximately 2.5 cm proximate of the second distal tip 136. The first catheter 110 is preferably an arterial lumen used to draw fluid, such as blood, from the patient, while the second catheter 130 is preferably a venous lumen used to return the fluid to the patient after processing, such as by hemodialysis. The approximate 2.5 cm distance difference between the first distal tip 116 and the second distal tip 136 serves to reduce recirculation of the fluid that has already been processed.

As shown in FIG. 2, in the cannulating portion 102 of the multiple catheter assembly 100, each of the first catheter 110 and the second catheter 130 comprise semicircular cross-sections 128, 148, respectively. Accordingly, the first outer surface 120 is defined by a first generally flat portion 124 and a first rounded wall portion 125. Likewise, the second outer surface 140 is defined by a second generally flat portion 144 and a second rounded wall portion 145. Preferably, the first generally flat portion 124 and the second generally flat portion 144 are juxtaposed from each other and are very close to each other, but do not necessarily touch each other. It is also preferable that the first outer surface 120 and the second outer surface 140 are virtually identical to each other so that when the first generally flat portion 124 is very close to the second generally flat portion 144, the outer surface 104 of the cannulating portion 102 has a generally circular cross section 106. It should be understood, based on this disclosure, that the first catheter 110 and the second catheter 130 may be further subdivided and/or additional catheter tubes of the same or varied cross sectional configuration may be provided within the scope of the invention.

The multiple catheter assembly 100 includes a splittable bond 180, which extends longitudinally between and joins the first generally flat portion 124 and the second generally flat portion 144. The splittable bond 180 may be an adhesive used to releasably connect the first generally flat portion 124 and the second generally flat portion 144.

While the generally semi-circular cross section 128, 148 of the first catheter 110 and the second catheter 130 as shown in FIG. 2 corresponding to the cannulating portion 102 of the multiple catheter assembly 100 is the preferred configuration for fluid flow in each of the first lumen 122 and second lumen 142, other configurations may be used without departing from the spirit of the present invention, such as, for example, oval, circular, elliptical, square, triangular, and kidney-bean shaped. A multiple catheter assembly having such luminal configurations may have an accordingly varied cross section. The first lumen 122 and second lumen 142 may be of equal cross sectional or of different cross sectional areas.

While two lumens 122, 142 of equally sized cross sections are shown in FIGS. 2-4, additional catheters having lumens of the same or different cross sectional areas may also be included in the multiple catheter assembly 100. For example, a multiple catheter assembly 100 used for hemodialysis may comprise two catheters of equal cross sectional area for the removal and return of blood and a third catheter with a smaller cross sectional area to be used for the infusion of medication into the patient. In such an embodiment, it is preferable to have the catheters connected by more than one splittable bond. The catheter assembly with such a configuration may also not be circular in cross section in a configuration having unequal cross sectional areas.

It is also possible to subdivide the various catheter lumens 110, 130 within the assembly 100 by providing at least one longitudinally extending septum within a lumen. In this manner, by having a longitudinally extending septum, a dual catheter assembly can provide three or more individual lumens by splitting the individual catheter(s). These and all of the alternative tube configurations are intended to be merely exemplary and illustrative, and by no means is this an inclusive list. It will be understood that the present invention is not limited to the configurations shown or mentioned in this specification or shown in the drawings.

Referring back to FIG. 1, the distal tip of the first catheter 110 includes the first distal opening 118 extending therethrough. Likewise the distal tip 136 of the second catheter 130 includes the second distal opening 138 extending therethrough. Preferably, the distal tips 116, 136 are blunt, in that they are configured to lie generally in a plane which is perpendicular to the longitudinal length of the cannulating portion 102. The distal tips 116, 136 may have a semicircular cross section or a slightly circular cross section. However, in the present embodiment, referring to FIGS. 3 and 4, the distal tips 116, 136 comprise a first distal generally oval cross section 117 and a second distal generally oval cross section 137. However, those skilled in the art will recognize that the distal tips 116, 136 may include cross sections of other shapes, such as round, or other suitable shapes. Referring to FIG. 1, it is preferred that the distal tips 116, 136 have a distal transition portion 119, 139, respectively, wherein the cross section transitions from semi-circular, proximally of each distal transition portion 119, 139, to oval, distally of each distal transition portion 119, 139. A plurality of side apertures 194 are located throughout the first distal end region 114 and the second distal end region 134. Specifically, in the preferred embodiment, the plurality of side apertures 194 are located on the first and second generally oval cross sections 117, 137, respectively, although those skilled in the art will recognize that the side apertures may also or alternatively be located on the first and second generally semi-circular cross-sections 128, 148 just proximal of each of the distal tips 116, 136. The side apertures 194 on the first semi-circular cross-section are in fluid communication with the first lumen 122 and the side apertures 194 on the second semi-circular cross-section are in fluid communication with the second lumen 142.

Figure 5:
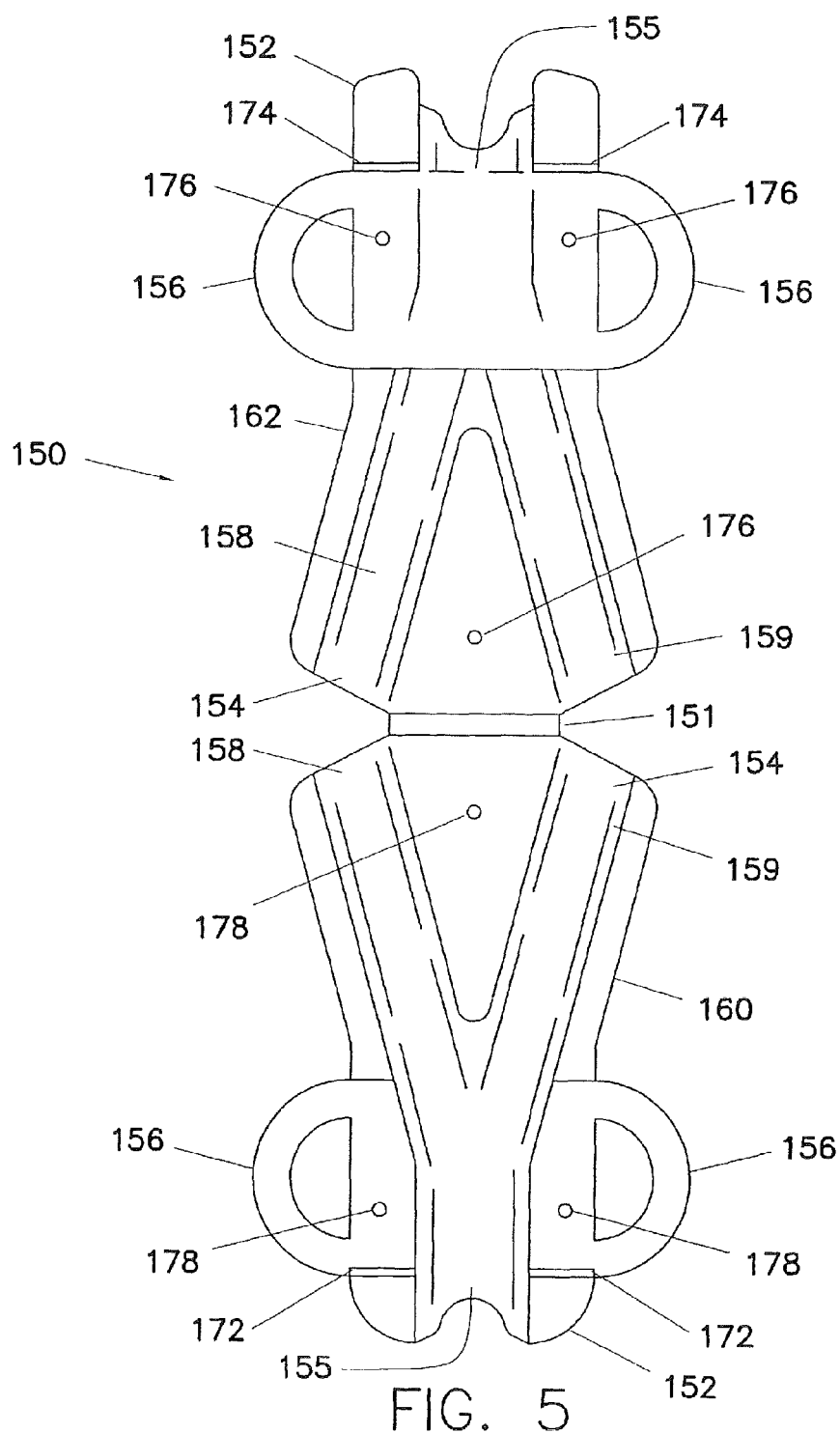
FIG. 5 is an enlarged top plan view of a catheter hub according to an embodiment of the present invention in an open position.
Figure 6:
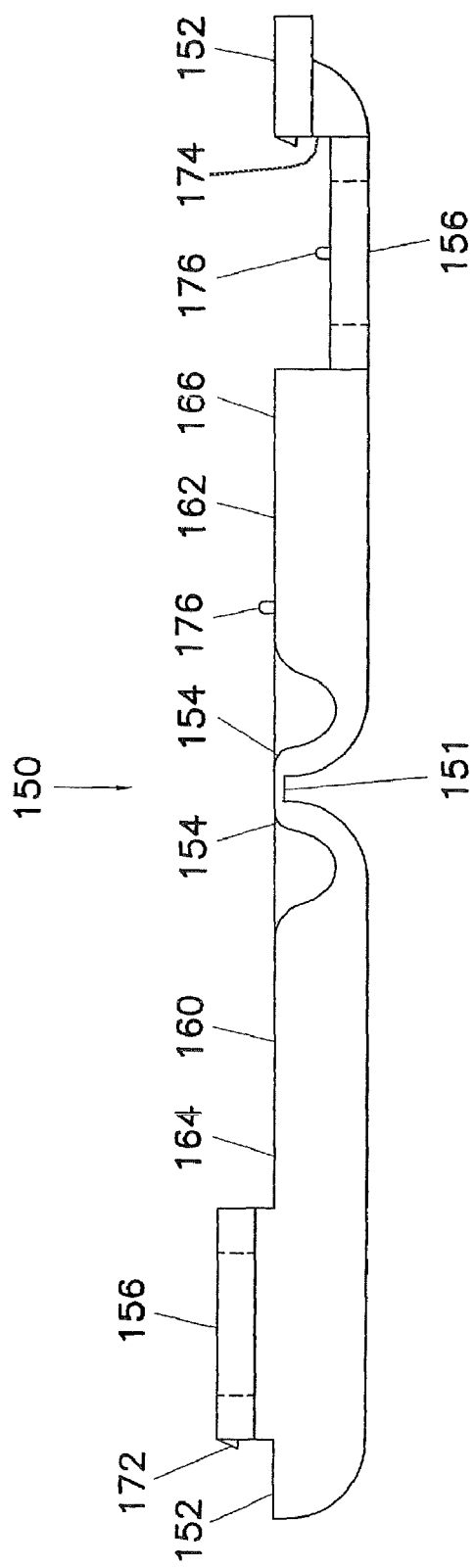
FIG. 6 is a side view of the hub of FIG. 5.

Still referring to FIG. 1, a longitudinally translatable hub 150 is releasably connected to the proximal regions 112, 132 of the first and second catheters 110, 130, respectively. A preferred hub 150 is disclosed in U.S. Pat. No. 7,261,708, which is incorporated by reference herein in its entirety as though fully set forth, although those skilled in the art will recognize that other hub designs may be used, or that the hub 150 may be omitted in its entirety. The hub 150, as shown in FIGS. 1, 5, and 6, is operable between an open position and a closed position and has a distal end 152 and a proximal end 154. The hub 150 is designed to allow both of the catheters 110, 130 in the multiple catheter assembly 100 to enter the distal end 152 of the hub 150 together. A distal channel 155 runs longitudinally through the hub 150 to house the catheters 110, 130. At a predetermined point along the hub 150, the distal channel 155 branches out, from the single distal channel 155, near the distal end 152 of the hub 150, to a first proximal channel 158 and a second proximal channel 159 near the proximal end 154 of the hub 150. Each of the first proximal and second proximal channels 158, 159 houses one or more individual catheters 110, 130 but less than the number of catheters housed by the distal channel 155. In the present embodiment, as shown in FIGS. 1, 5, and 6, the distal end 152 of the hub 150 is designed to juxtapose the first catheter 110 and second catheter 130 against each other and the proximal end 154 of the hub 150 is designed to separate the first catheter 110 from the second catheter 130. The hub 150 may also be slid longitudinally along the multiple catheter assembly 100. The distal channel 155 and the first and second proximal channels 158, 159 of the hub are sized so that the hub 150 may frictionally maintain its place on the multiple catheter assembly 100.

Referring to FIGS. 5 and 6, the hub 150 comprises a top hub portion 160 and a bottom hub portion 162. The top and bottom hub portions 160, 162 are hingedly connected by a hinge 151 at the proximal end 154 of the hub 150. The hinge 151 is located between the first proximal channel 158 and the second proximal channel 159. The top hub portion 160 is adapted to mate to the bottom hub portion 162, when the hub 150 is in a closed position. The distal channel 155 and the first and second proximal channels 158, 159 are partially disposed on the inner face 164 of the top hub portion 160 as well as on the inner face 166 of the bottom hub portion 162 so that when the hub 150 is in the closed position, the inner face 164 of the top hub portion 160 mates with the inner face 166 of the bottom hub portion 162 and the distal and first and second proximal channel 155, 158, 159 run through the hub 150. The hub 150 releasably locks in the closed position. The top hub portion 160 includes tabs 172, which snap into recesses 174 in the bottom hub portion 162. The tabs 172 and recesses 174, as well as raised bumps 176 on the bottom hub portion 162, which mate to small indentations 178 on the top hub portion 160, ensure the rigidity of the hub 150 when in the closed position. Although a snapping tab and recess mechanism is disclosed here, this invention anticipates a wide array of means for releasably locking the top hub portion 160 and the bottom hub portion 162 in the closed position.

The hub 150 is releasably attachable to a patient. The hub 150 includes a plurality of suture wings 156 protruding therefrom, which may be releasably attached to a patient. The suture wings 156 protrude from the hub 150 on either side of the distal channel 155 as shown in FIG. 5. Four suture wings 156 are positioned on the top hub portion 160 and the bottom hub portion 162 such that when the hub 150 is in the closed position, the four suture wings 156 align to form two suture wing assemblies 157, shown in FIG. 1. In the present embodiment, the suture wing assemblies 157 are adjacent to the tabs 172 and recesses 174, but they may be located anywhere on the hub 150. With the suture wing assemblies 157 located in a position away from the hinge 151, they can be used to assist in securing the hub 150 in the closed position. Furthermore, this invention anticipates other means for releasably attaching a hub 150 to a patient. Further, while two suture wing assemblies 157 are shown in FIG. 1, those skilled in the art will recognize that more or less than two suture wing assemblies 157 may be used.

Figures 7, 8:
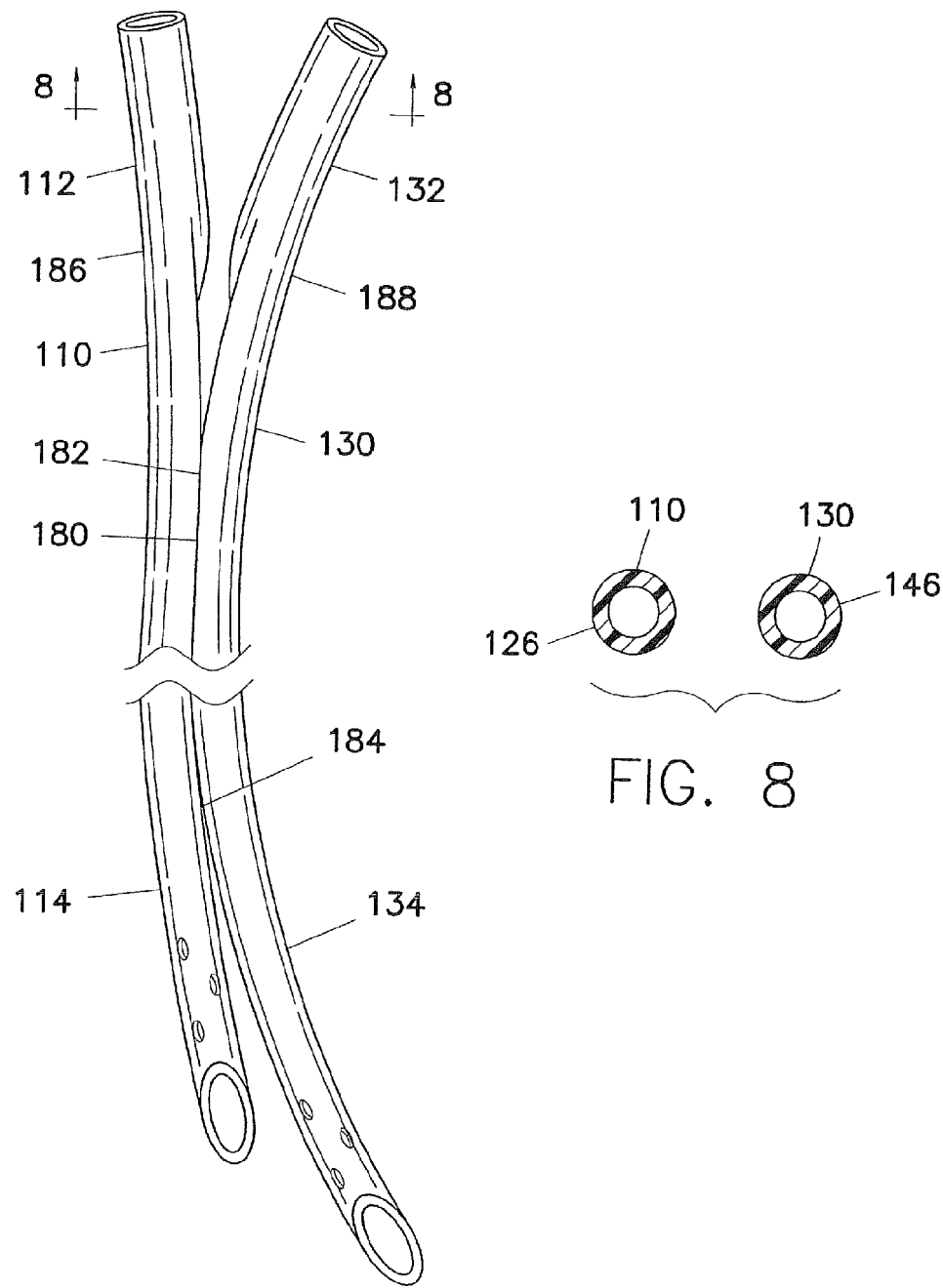
FIG. 7 is a top plan view of the catheters only from the catheter assembly of FIG. 1.
FIG. 8 is a sectional view of the catheters taken along lines 8-8 of FIG. 7.

Referring now to FIG. 7, which shows the catheters 110, 130 only, a splittable bond 180 releasably connects the first catheter 110 to the second catheter 130 in the cannulating portion 102 thereof. The splittable bond 180 includes a distal end 184 and a proximal end 182, either or both of which may be split to allow the proximal end regions 112, 132 and the distal end regions 114, 134 of the first catheter 110 and second catheter 130, respectively, to be manipulated independently of each other.

The splittable bond 180 performs multiple functions. First, the splittable bond 180 joins the first catheter 110 and the second catheter 130 so that the first catheter 110 and second catheter 130 may be easily manipulated together, particularly along the section of the first catheter and second catheter 130 where the splittable bond 180 is unbroken. If the splittable bond 180 is intact, the first catheter 110 and the second catheter 130 may be manipulated as a single catheter. Second, the splittable bond 180 allows the first catheter 110 and the second catheter 130 to be at least partially longitudinally split apart from each other without damaging the outer surface of the first catheter 110 or the second catheter 130. Splitting the distal end 184 of the splittable bond 180 allows independent movement of the first distal end region 114 and the second distal end region 134 in the vessel or other area to be catheterized. Conversely, splitting the proximal end 182 of the splittable bond 180 allows independent movement of the first proximal end region 112 and the second proximal end region 132. Such independent movement allows for longitudinal translation of the hub 150 (not shown in FIG. 7) along a length of the catheter assembly 100. The splittable bond 180 is constructed to split easily when the first catheter 110 and the second catheter 130 are forcibly pulled apart from each other. It is preferred, as shown in FIG. 2, that the splittable bond 180 has a cross sectional width "w" at its thinnest point which is a very small fraction of the outer diameter of the multiple catheter assembly 100 to facilitate easy tearing.

The splittable bond 180 is also constructed of a material, such as an adhesive, that will tear before the forces exerted in the outer surfaces of either the first catheter 110 or second catheter 130 reach a level that will cause damage thereto. However, the splittable bond 180 should be sufficiently strong to resist tearing during normal handling of the multiple catheter assembly 100. The splittable bond 180 has a cross sectional length "l" which is also a small fraction of the outer diameter of the multiple catheter assembly 100. The cross sectional length "l" of the splittable bond 180 also defines the distance between the first generally flat surface 124 and the second generally flat surface 144. The cross sectional length "l" of the splittable bond 180 is preferably small enough to maintain an overall generally circular cross section 104, and to facilitate handling of the unseparated cannulating portion 102 of the multiple catheter assembly 100.

Referring back to FIG. 7, the proximal portion 112, 132 of each of the first and second catheters 110, 130 includes a first transition portion 186 and a second transition portion 188, respectively. These transition portions 186, 188 comprise a change in the cross sectional profile of the first and second catheters 110, 130. Specifically, distally of the first transition portion 186, the first catheter 110 has a generally semi-circular cross section 128, as shown in FIG. 2, whereas proximally of the first transition portion 186, the first catheter 110 has a generally oval cross section 126, as shown in FIG. 8. Similarly, distally of the second transition portion 188, the second catheter 130 has a generally semi-circular cross section 148, whereas proximally of the second transition portion 188, the second catheter 130 has a generally circular cross section 146. The first transition portion 186 and second transition portion 188 are located in the very near proximity of the proximal end 182 of the splittable bond 180. The first generally flat surface 124 and second generally flat surface 144, that are joined by the splittable bond 180, each end at the first transition portion 186 and second transition portion 188.

Referring back to FIG. 1, a first extension tube assembly 113 and a second extension tube assembly 133 are attached to the first proximal end 111 and the second proximal end 131, respectively. For illustrative purposes, the first extension tube assembly 113 is shown in an exploded view in FIG. 9. While an exploded view of the second extension tube assembly 133 is not shown, those skilled in the art will recognize that the second extension tube assembly 133 includes the same components as the first extension tube assembly 113.

Each extension tube assembly 113, 133 includes an extension tube 196, a luer connector 198 connected to a proximal end of each extension tube 196, and a male threaded connector portion 200 connected to a distal end of each extension tube 196. A clamp 202, such as a Roberts clamp, or some other suitable clamp known to those skilled in the art, is disposed over each extension tube 196 between each luer connector 198 and each male threaded connector portion 200. Each clamp 202 is operable between an open condition that allows fluid flow through each respective extension tube 196 and a closed condition that precludes fluid flow through each respective extension tube 196.

An extension tube connector 204 extends from each male threaded connector portion 200. Each extension tube connector 204 is sized to be inserted into the proximal end openings 111, 131 of each of the first catheter 110 and the second catheter 130, respectively. A barb 205 may extend from the tube connector 204 to retain the proximal end 112, 132 of each of the first and second lumens 110, 130, although those skilled in the art will recognize that more than one barb 205 may be used, or that the barb 205 may be omitted in its entirety. A compression fitting 206 is disposed over the exterior of each catheter 110, 130 and over each extension tube connector 204. A female threaded connector portion 208 is disposed over each compression fitting 206 and is threadedly connected to each respective male threaded connector portion 200, securing each extension tube assembly 113, 133 to each respective catheter lumen 110, 130 and providing for fluid communication between the extension tube assemblies 113, 133 and each respective catheter lumen 110, 130.

Referring back to FIG. 1, a fabric cuff 125 is disposed on a portion of the exterior of the catheters 110, 130, preferably approximately halfway between the proximal end regions 112, 132 and the distal end regions 114, 134 of the catheters 110, 130. The portion of the catheter 110, 130 located distal of the cuff 125 are inserted into the patient through an incision during catheterization, and the portion of the catheters 110, 130, as well as the remaining portions of the catheter assembly 100, remain exterior of the incision. The cuff 125 provides a surface for the patient's skin to graft to the catheter assembly 100. Preferably, the cuff 125 is constructed from DACRON® polyester or some other, suitable, biocompatible fabric.

Preferably, the first and second catheters 110, 130 are constructed from a biocompatible polyurethane, such as TECOTHANE® or CARBOTHANE® polyurethanes, although those skilled in the art will recognize that other materials, such as biocompatible plastics such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art may be used. It should be understood that these possible biocompatible materials are included above for exemplary purposes and should not be construed as limiting. If a biocompatible polymeric material is used to form the first and second catheters 110, 130, it is most preferred that the polymeric material includes a polyurethane or a polyolefin polymeric material having a preferably soft durometer.

Other suitable, preferred, biocompatible elastomers for use in forming the catheters 110, 130 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the catheters 110, 130 are made of the elastomeric material such that they are flexible, durable, soft, and easily conformable to the shape of the area to be catheterized and/or a subcutaneous area and minimize risk of harm to vessel walls. If the catheters 110, 130 are used for hemodialysis applications, they are preferably formed of a soft silicone elastomer which has a hardness of at least about 80-A on a Shore durometer scale. Such an elastomer is available from Dow Corning, and can include 20% barium sulfate in the elastomer to provide radiopacity. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the catheters 110, 130 may also be radiopaque depending on their intended use.

In one preferred embodiment of the present invention, the cannulating portion 102 of the assembly 100 is fabricated by a single extrusion process, injection molding process, or blow molding process. One fabrication process is extrusion. In such a process, the splittable bond 180 may be formed using the same material as the catheters 110, 130. In an alternative embodiment, each catheter 110, 130 and the bond 180 are individually formed, and then joined by suitable manufacturing techniques to become a unitary product. In this alternative process, the bond 180 may be formed of the same, or different material than the catheters 110, 130, such as an adhesive.

Figure 10:
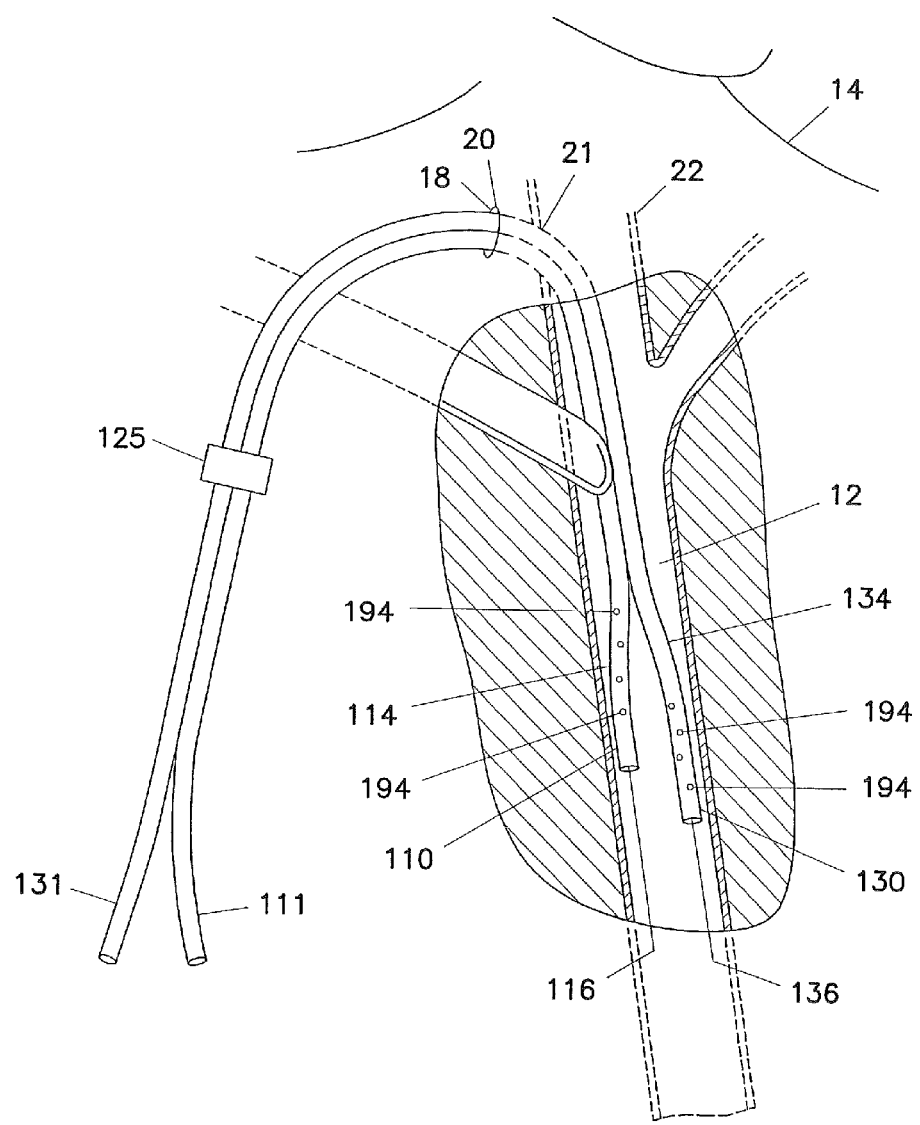
FIG. 10 is a partially broken away diagrammatic view of a multiple catheter assembly which has been partially split and inserted into an area to be catheterized, in accordance with one embodiment of inserting a multiple catheter assembly according to the present invention.
Figure 11:
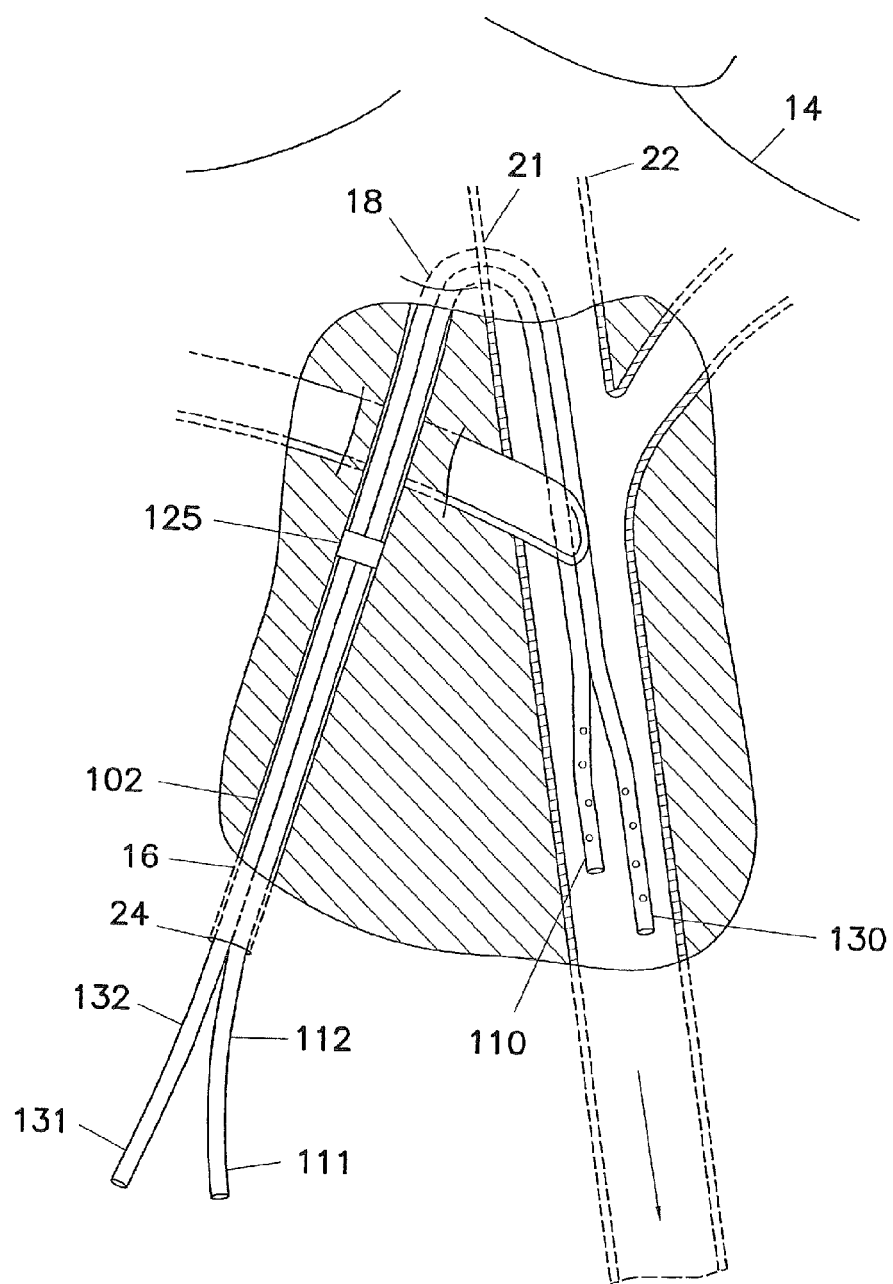
FIG. 11 is a partially broken away diagrammatic view of the multiple catheter assembly of FIG. 10, with a proximal portion of the catheter assembly having been subcutaneously tunneled, in accordance with one embodiment of inserting a multiple catheter assembly according to the present invention.
Figure 12:
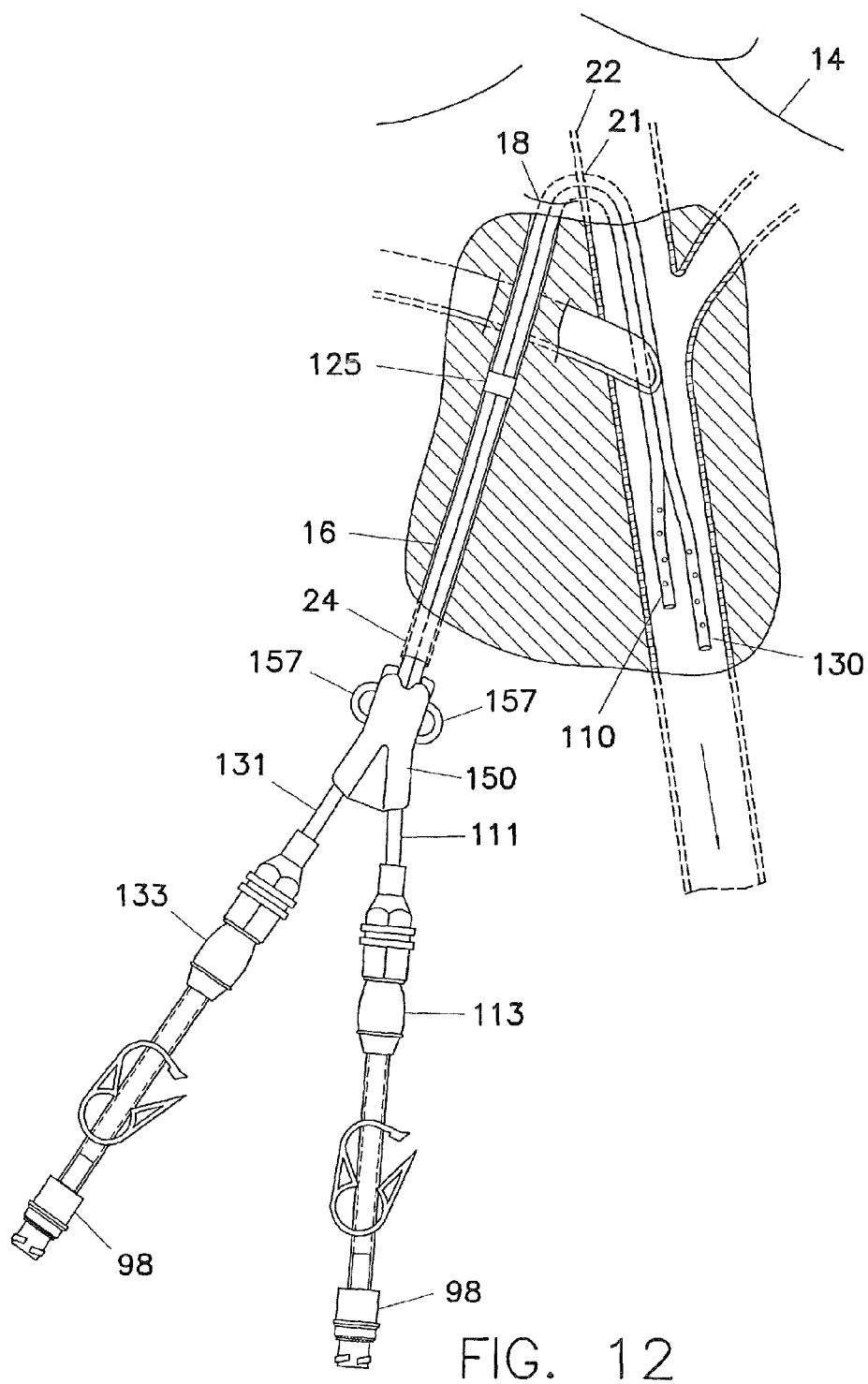
FIG. 12 is a partially broken away diagrammatic view of the multiple catheter assembly of FIG. 10, with a hub and catheter extension connected to the proximal portion of the catheter assembly, in accordance with one embodiment of inserting a multiple catheter assembly according to the present invention.

A preferred method of insertion of the catheter assembly 100 is shown graphically in FIGS. 10 through 12. The catheter assembly 100 is devoid of the hub 150 and the extension tube assemblies 113, 133, so that the catheter assembly 100 appears as shown in FIG. 7. Referring now to FIG. 10, an incision 18 is initially made near an insertion site 20 which is to be aspirated with a syringe or other introducer apparatus near or proximate the area to be catheterized 21 on the patient 14. If the catheter assembly 100 is used for hemodialysis and the area to be catheterized 21 is the internal jugular vein 22, the incision 18 is made in the clavicular triangle region, as shown for example, in FIG. 10. The exact location of the incision 18 may be varied by the surgeon. In accordance with the Seldinger technique, a narrow needle is inserted through the incision 18 and into the vein 21, and the vein 22 is aspirated. A guide wire (not shown) is then passed through the needle, or other introducer, and the needle is removed. A dilator (not shown) and a tearable sheath are introduced over the guide wire and partially into the vein 22. Once the sheath is in place, the dilator and the guide wire are removed, leaving the sheath in place. The insertion site 18 is now ready to accept the catheter assembly 100.

Prior to insertion, the catheter assembly 100 is split along the splittable bond 180 from the distal tip 116 of the first catheter 110 by a longitudinal distance which is at least long enough to allow free flow through all side apertures 194. Preferably, the bond 180 is split along a length of the catheters 110, 130 as desired by the surgeon, up to the ingrowth cuff 125. Preferably, the catheters 110, 130 are already at least partially split along a portion of the distal end regions 114, 134 of the catheters 110, 130 as shown in FIG. 1 prior to insertion, which facilitates splitting of the splittable bond 180. While the user does not have to split the entire length of the bond 180, it is preferred that the bond 180 be fully split for allowing independent movement of the distal end regions 114, 134 of the catheters 110, 130 within the vessel.

After splitting, the distal end regions 114, 134 of the first and second catheters 110, 130 are inserted into, and through, the sheath in juxtaposed relationship. The distal end regions 114, 134 are inserted until they are properly positioned within the area 12, as shown in FIG. 10. The sheath is then removed in the conventional manner, leaving the distal end regions 114, 134 of the first and second catheters 110, 130 in the area 12. As shown in FIG. 10, at least a portion of the distal end regions 114, 134 of each of the catheters 110, 130 may freely move within the area 12.

Referring to FIG. 11, the proximal portions of the catheters 110, 130 may be optionally located within a subcutaneous tunnel 24 in the subcutaneous area 16 of the body 14, using various tunnelling techniques. In one preferred technique, the proximal end regions 112, 132 of the catheters 110, 130 are pulled through the tunnel 24 from the end of the tunnel 24 proximate to the incision 18, while forming the tunnel 24 using a trocar or other tunnelling tool, leaving the proximal end regions 112, 132 at least partially within the tunnel 24, with the proximal ends 111, 131 extending beyond the tunnel 24.

A catheter tunneling adapter 210, preferably similar to the catheter tunneling adapter shown in FIG. 13 and disclosed in U.S. Patent Publication No. US 2004/0176739, is releasably connected to the proximal ends 111, 131 of the catheters 110, 130. Alternatively, an adapter such as the adapter disclosed in U.S. Patent Publication No. US 2005/0027282 may be used. Preferably, an extension 211 extending from the first end 212 of the tunneling adapter 210 is inserted into each of the proximal ends 111, 131 of the catheters 110, 130 and a trocar 214 is connected to the second end 216 of the adapter 210. The trocar 214, the adapter 210, and catheters 110, 130 are pulled through the subcutaneous tunnel 24 made by the pointed end 218 of the trocar 214. Once the catheters 110, 130 have been placed in the subcutaneous tunnel 24, and after the adapter 210 and trocar 214 have been removed, the catheters 110, 130 appear as shown in FIG. 11. The ingrowth cuff 125 is disposed within the subcutaneous tunnel 24. Over time, skin tissue forming the wall of the subcutaneous tunnel 24 will grow into the ingrowth cuff 125, securing the catheters 110, 130 in the subcutaneous tunnel 24.

After the catheter assembly 100 is inserted as shown in FIG. 11, the incision 18 is closed and the cannulating portion 102 of the assembly 100 is substantially below the skin of the patient. Next, the extension tube assemblies 113, 133 are connected to the proximal ends 111, 131 of the first and second catheters 110, 130, respectively.

Figure 9:
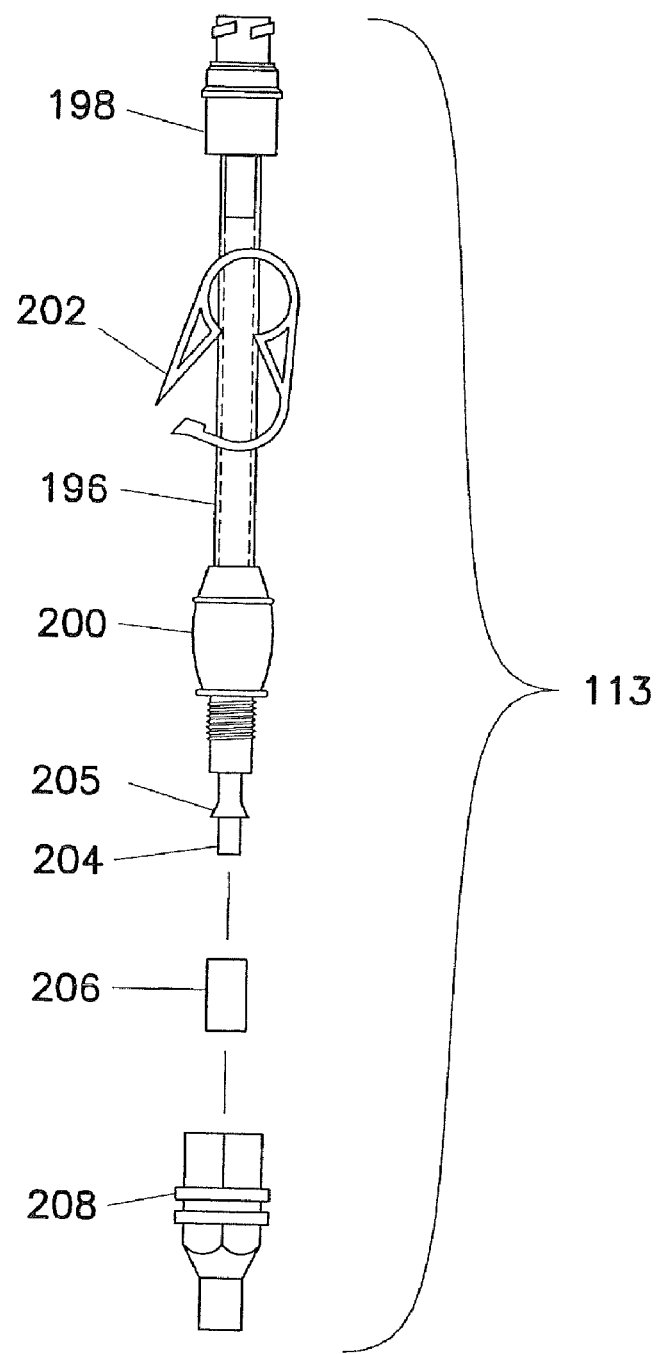
FIG. 9 is an enlarged exploded view of an extension tube assembly according to an embodiment of the present invention.

Regarding the first extension tube assembly 113 and referring to FIGS. 8 and 9, the first female threaded connector portion 208 is first slid over the exterior of the proximal end 111 of the first lumen 110. Next, the first compression fitting 206 is slid over the exterior of the proximal end 111 of the first lumen 110. Then, the first extension tube connector 204 is inserted into the proximal end 111 of the first catheter 110. The first female threaded connector portion 208 is threadingly connected to the first male threaded connector portion 200, such that the compression fitting 206 and the proximal end 111 of the first catheter 110 are securely retained between the first female threaded connector portion 208 and the first extension tube connector 204. The process is repeated for connecting the second extension tube assembly 133 to the second catheter 130.

Now with reference to FIGS. 5 and 6, to further ensure that the proximal catheter end regions 112, 134 remain secured in the subcutaneous area 16 of the body 14, the hub 150 is secured to the assembly 100 by placing the catheters 110, 130 into the bottom hub portion 162 such that the first transition portion 186 is disposed in the first proximal channel 158 and the second transition portion 188 is disposed in the second proximal channel 159, with a portion of the first and second catheters 110, 130 distal of the first and second transition portions 158, 159 being disposed within the distal channel 155. The top hub portion 160 is pivoted about the hinge 151 to the closed position such that the tabs 172 on the top hub 160 portion snap into the recesses 174 in the bottom hub portion 162, securing the hub 150 to the catheters 110, 130. The hub 150 may now be sutured to the patient's skin by suturing the sutures (not shown) over the suture wing assemblies 157. Insertion of the catheter assembly 100 is now complete, as shown in FIG. 12.

Lastly, the open ends of the luer connectors 198, extending caudally from the tunnel 24, are attached in fluid communication with respective fluid inlets and outlets of a hemodialysis unit, or other fluid transfer equipment (not shown), and dialysis can begin.

After the catheter assembly 100 has been inserted into the patient for sufficient time for the ingrowth cuff 125 to become secured within the subcutaneous tunnel 24, the sutures may be cut from the suture wing assemblies 157. The hub 150 may be removed by unsnapping the tabs 172 in the top hub portion 160 from the recesses 174 in the bottom hub portion 162, pivoting the top hub portion 160 about the hinge 151 to open the hub 150, and removing the hub 150 from the rest of the catheter assembly 100.

In an alternative insertion method, the catheters 110, 130 are pulled through the subcutaneous tunnel 24 prior to inserting the distal ends 114, 124 of the catheters 110, 130 into the vessel being catheterized. In this method, the catheter tunneling adapter 210 is connected to the distal ends 114, 134 of the catheters 110, 130 and the pointed end 218 of the trocar 214 is used to form the subcutaneous tunnel 24 and to pull the catheter lumens 110, 130 through the tunnel 24. The pointed end 218 of the trocar 214 exits the skin proximate to the insertion site 20. The trocar 214 and the catheter tunneling adapter 210 are removed and the distal ends 214, 234 of the catheters 210, 230 are inserted into the incision 18 as described above. The extension tube assembles 113, 133 may be connected to the proximal ends 111, 131 of the catheters 110, 130 prior to or after inserting the catheters 110, 130 into the vessel.

An alternate embodiment of a catheter assembly 300 according to the present invention is shown in FIGS. 14 to 17, 19 and 20. The catheter assembly 300 is preferably similar to the catheter assembly 100 as described above, but with additional or different features as are described below.

The catheter assembly 300 includes first and second catheters 310, 340 that are bonded to each other over a portion of their lengths. Preferably, the first catheter 310 is referred to as the arterial catheter, and is used to draw fluid from the patient's body. Also preferably, the second catheter 340 is referred to as the venous catheter and is used to return or to administer fluid to the patient.

Figures 14, 15:
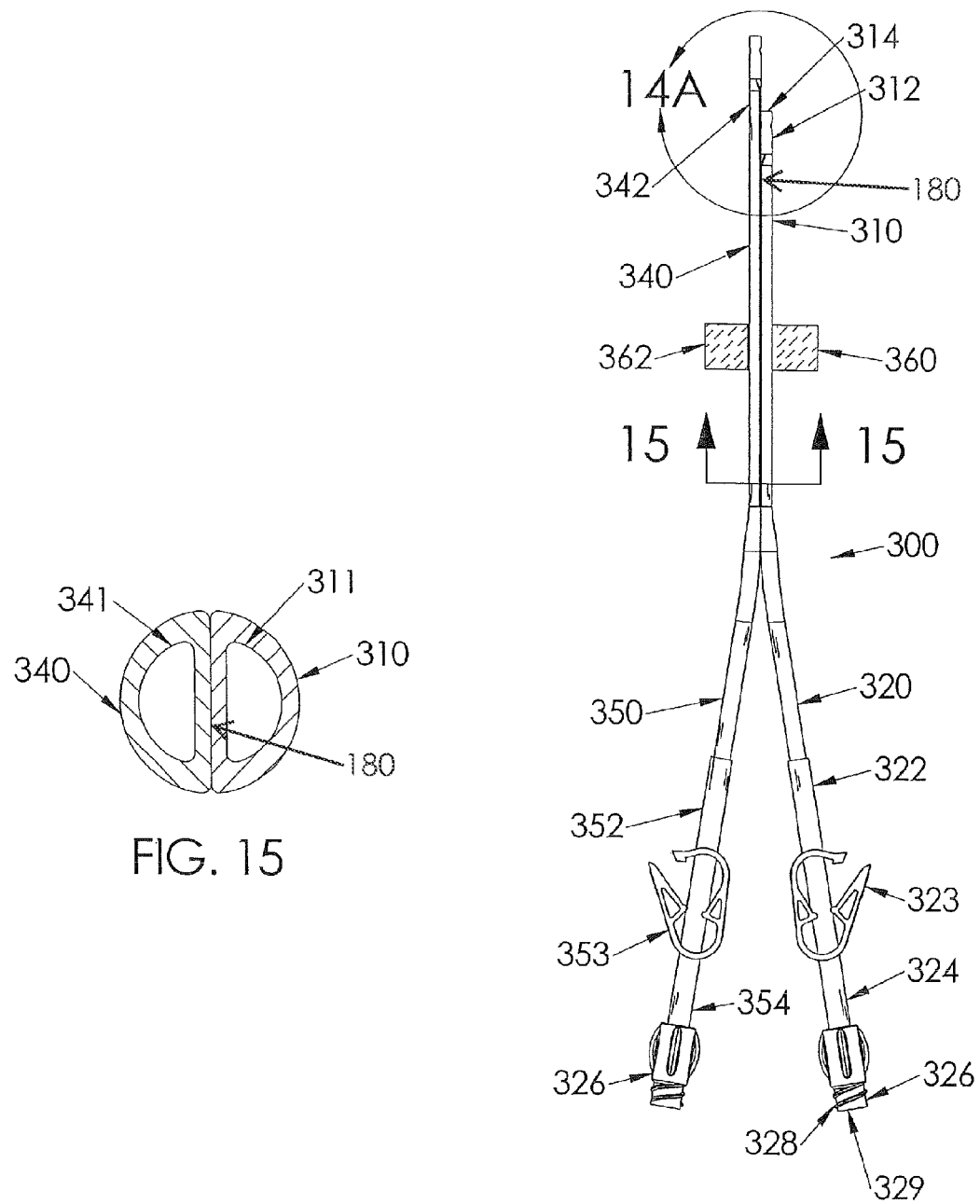
FIG. 14 is a top plan view of a catheter assembly according to a second preferred embodiment of the present invention.
FIG. 15 is an enlarged sectional view of the catheter lumens of the catheter assembly taken along lines 15-15 of FIG. 14.

Preferably, the bonded portion of the first catheter 310 has a generally "D-shaped" cross-section, as shown in FIG. 15. The first catheter 310 includes a first lumen 311 that extends therethrough. As seen in FIG. 15, a cross-section of the first lumen 311 is preferably generally "D-shaped" as well, although those skilled in the art will recognize that the cross-section of the first lumen 311 may be other shapes, such as round, oval, kidney-shaped, or other suitable shape.

Figure 14A:
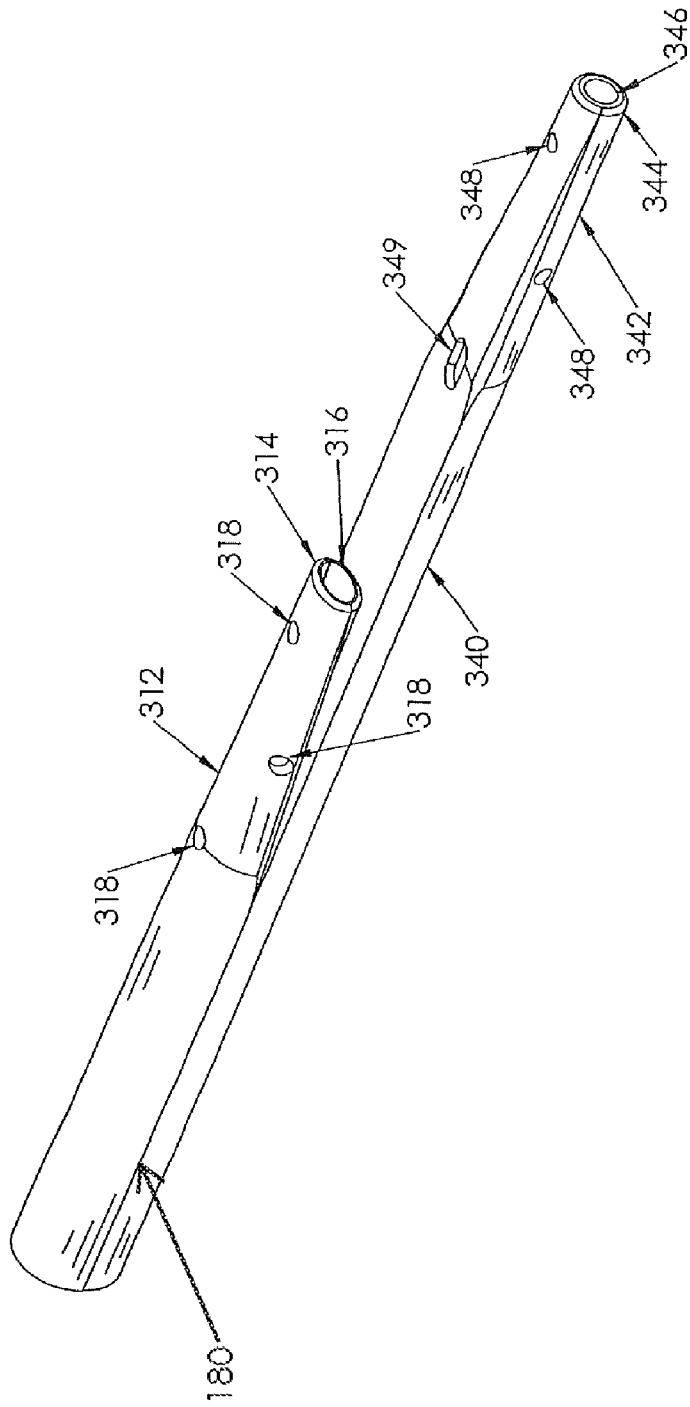
FIG. 14a is an enlarged perspective view of the distal end of the catheter assembly shown in FIG. 14.
Figure 16:
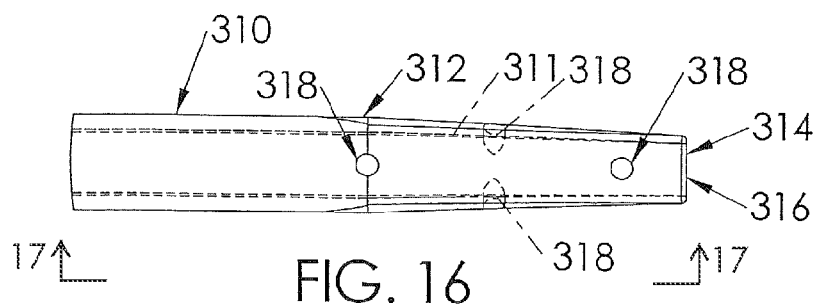
FIG. 16 is a top plan view of the distal end of the arterial catheter of the catheter assembly of FIG. 14.
Figure 17:
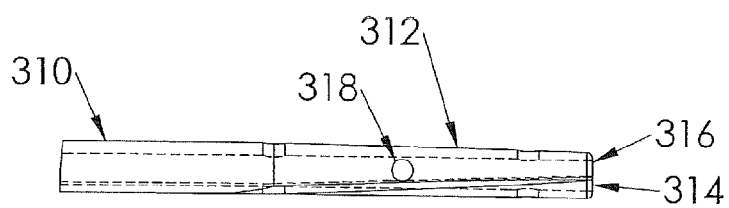
FIG. 17 is a side view of the distal end of the arterial catheter of FIG. 16.

Referring to FIGS. 14A, 16 and 17, the first catheter 310 includes a distal end 312 having a distal tip 314. At the distal end 312, the cross-section of the exterior of the first catheter 310 and of the first lumen 311 changes from the D-shape to an oval shape, with the cross-section of the distal tip 314 also being oval shaped. It is preferred that the distal tip 314 is oval to provide a larger flow area, which allows higher flow at lower pressure. Further, the oval shape aids in the manufacture of the first catheter 310, since the distal tip 314 can be inserted into a tipping mold without the need to insert a rod the entire length of the first lumen 311. The rod only needs to be inserted from the distal end 312 for a distance necessary to shape the distal tip 314 into the oval shape. Additionally, it is believed that the oval shape may be less prone to clotting in between uses.

A distal tip opening 316 is formed at the distal tip 314 to fluidly communicate between the first lumen 311 and the exterior of the first catheter 310. The distal tip 314 is preferably radiused between the first lumen 311 and the exterior of the first catheter 310 to prevent injury to a blood vessel during insertion of the catheter assembly 300 into a patient.

A plurality of side openings 318 are formed in the wall of the distal end 312. Preferably, the side openings 318 are longitudinally and helically spaced along the distal end 312. The side openings 318 allow for fluid flow through the first lumen 311 in the event that the distal tip 314 clogs due to clotting, or gets sucked against the wall of the vessel into which the catheter assembly 300 is inserted. Preferably, the side openings 318 are generally circular, although those skilled in the art will recognize that the openings 318 may be oval, or other shape as well.

Referring to FIG. 14, a proximal end 320 of the first catheter 310 has a cross-section that changes from the "D-shape" to a generally circular shape. Also, the cross-section of the first lumen 311 changes from the "D-shape" to a circular shape. The proximal end 320 of the first catheter 310 ends in a first extension tube 322 that is molded to the proximal end 320 of the first catheter 310. The first extension tube 322 is preferably constructed from a thermoplastic urethane elastomer, such as PELLETHANE® polyurethane, or some other suitable material. A first clamp 323 is disposed over the first extension tube 322. Preferably, the first clamp 323 is a Roberts clamp, or another suitable clamp known to those skilled in the art.

A proximal end 324 of the first extension tube 322 includes a luer fitting 326 that is connected to the first extension tube 322. The luer fitting 326 includes external threads 328 to threadingly connect to an external blood line (not shown), as well as a tapered passage 329 that provides fluid communication between the first extension tube 322 and the external blood line. The luer fitting 326 may be fixedly connected to the proximal end 324 of the first extension tube 322, such as by an adhesive or a solvent, or an alternative luer fitting 426, such as the luer fitting 426 shown in FIG. 18, may be releasably connected to the proximal end 324 of the first extension tube 322.

The luer fitting 426 includes a proximal portion 428 and a distal portion 430 that is threadingly connected to the proximal portion 428. The proximal portion 428 includes a cannula 432 that is sized to be inserted into the proximal end 324 of the first extension tube 322. The proximal portion 428 also includes male threads 434 that are disposed proximal of the cannula 432. The distal portion 430 includes female threads 436 that threadingly engage with the male threads 434 of the proximal portion 428.

Figure 18A:
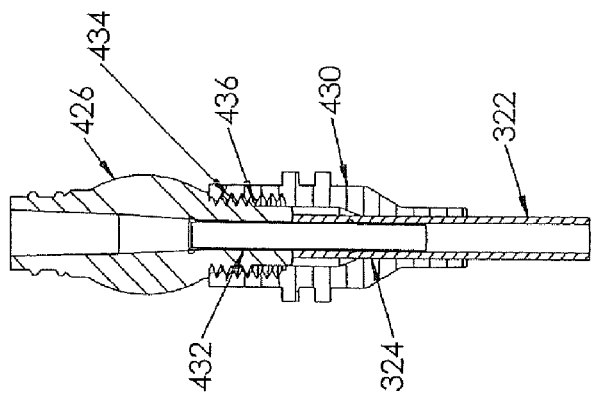
FIG. 18a is a side view, partially in section, of the luer connector of FIG. 18 connected to the proximal end of a catheter of the catheter assembly of FIG. 14.
Figure 18:
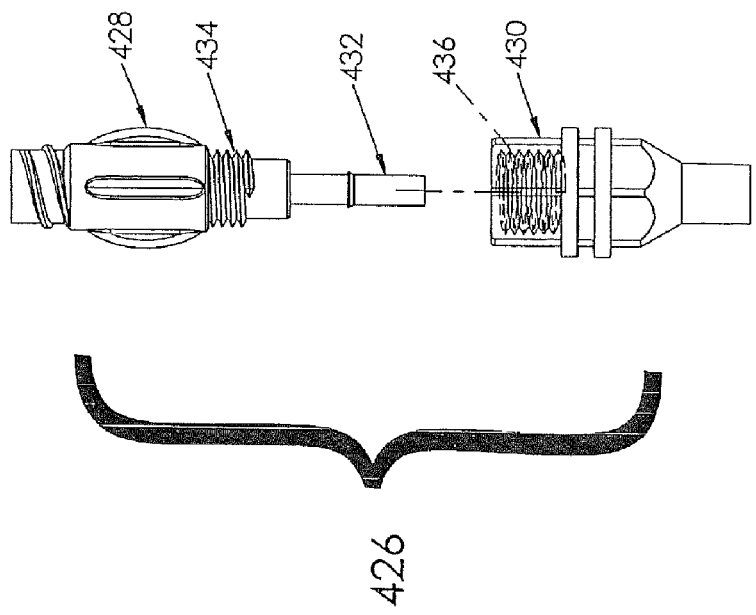
FIG. 18 is an exploded side view of an alternate luer connector for a proximal end of a catheter of the catheter assembly of FIG. 14.

As can be seen from FIG. 18a, distal portion 430 of the luer fitting 426 is disposed over the proximal end 324 of the first extension tube 322. The cannula 432 is next inserted into the proximal end 324 of the first extension tube 322 and the distal portion 430 of the luer fitting 426 is slid proximally along the first extension tube 322 so that the male and female threads 434, 436, respectively, are in engagement with each other. The insertable luer fitting 426 may be used when it is desired to retrograde tunnel the first extension tube 322 and the proximal end 320 through a subcutaneous tunnel during catheter insertion. The insertable luer fitting 426 may also be used to repair the catheter assembly 300, such as to replace a cracked or broken luer fitting 326 or to repair a cracked or broken extension tube 322.

Referring back to FIG. 14, the second catheter 340 is similar to the first catheter 310, but is longer in length at a distal end 342 than the distal end 312 of the first catheter 310. The second catheter 340 includes a second lumen 341 that extends therethrough, shown in FIGS. 19 and 20.

As seen in FIG. 15, a cross-section of the second lumen 341 is preferably generally "D-shaped" as well, although those skilled in the art will recognize that the cross-section of the second lumen 341 may be other shapes, such as round, oval, kidney-shaped, or other suitable shape. The second catheter 340 has a generally D-shaped body, with the flat part of the "D" being juxtaposed against the flat part of the "D" of the first catheter 310.

Referring back to FIGS. 14A, 19 and 20, the second catheter 340 includes a distal end 342 having a distal tip 344. At the distal end 342, the cross-section of the exterior of the second catheter 340 and of the second lumen 341 changes from the D-shape to a circular shape, with the cross-section of the distal tip 344 also being circular shaped. It is preferred that the distal tip 344 is circular to provide a smaller leading area during catheter insertion, since the second catheter 340 extends distally of the first lumen 310. This smaller leading area acts as a wedge as the catheter 300 is inserted into a blood vessel, which increases the mechanical advantage of the second catheter 340 as the second catheter 340 is inserted into the vessel. Additionally, during insertion, a stylet (not shown) may be inserted through the second catheter 340 to provide added rigidity to the second catheter 340. The rounded distal tip 344 provides minimal slack between the stylet and the interior of the second catheter 340 as opposed to an oval tip, which may deform due to excessive space between the stylet and the interior of the second catheter 340. Additionally, the rounded distal tip 344 extends for approximately one (1) centimeter, which it is believed helps maintain the rigidity of the distal tip 344 during insertion.

A distal tip opening 346 is formed at the distal tip 344 to fluidly communicate between the second lumen 341 and the exterior of the second catheter 340. The distal tip 344 is preferably radiused between the second lumen 341 and the exterior of the second catheter 340 to prevent injury to a blood vessel during insertion of the catheter assembly 300 into a patient.

Figure 19:
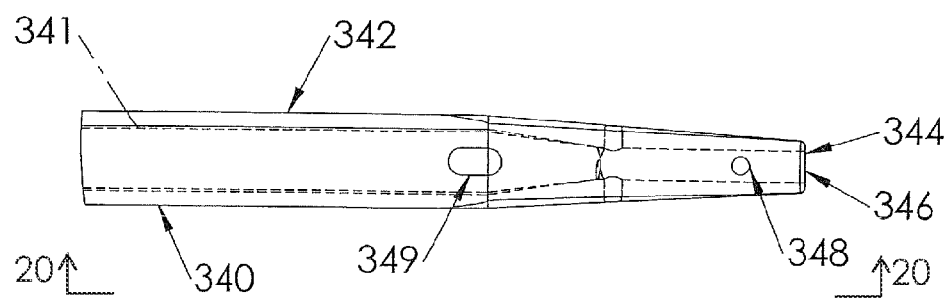
FIG. 19 is a top plan view of the distal end of the venous catheter of the catheter assembly of FIG. 14.
Figure 20:
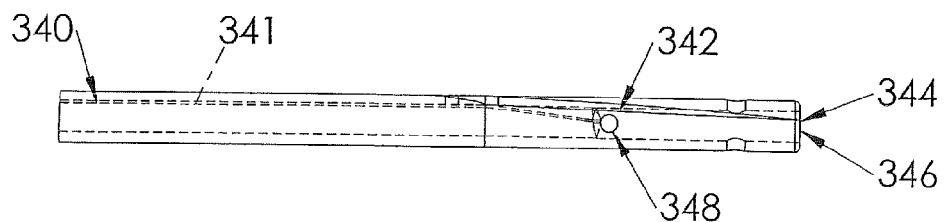
FIG. 20 is a side view of the distal end of the venous catheter of FIG. 19.
Figure 16A:
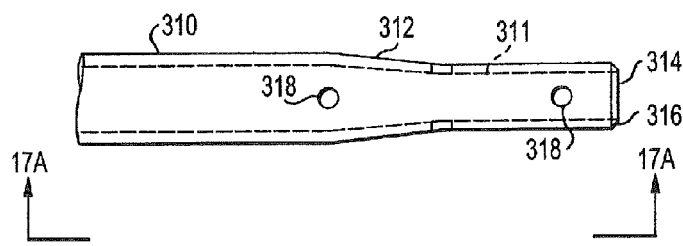
FIG. 16A is a top plan view of another embodiment of the distal end of the arterial catheter of the catheter assembly of FIG. 14.
Figure 17A:
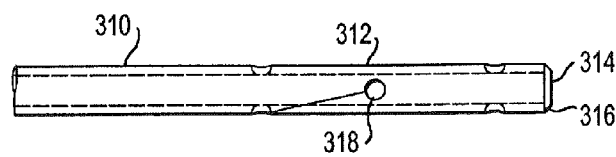
FIG. 17A is a side view of another embodiment of the distal end of the arterial catheter taken along lines 17A-17A of FIG. 16A.
Figure 19A:
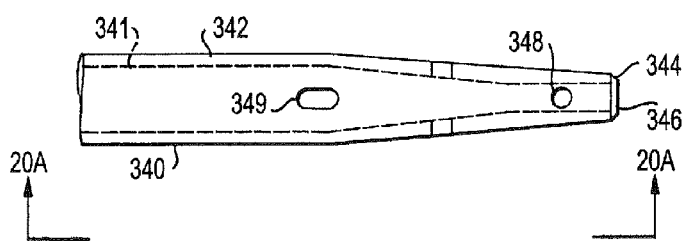
FIG. 19A is a top plan view of another embodiment of the distal end of the venous catheter of the catheter assembly of FIG. 14.
Figure 20A:
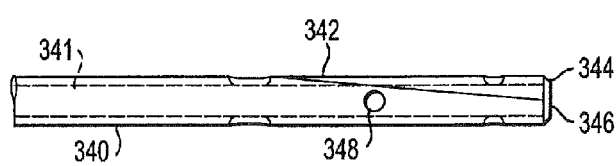
FIG. 20A is a side view of another embodiment of the distal end of the venous catheter taken along lines 20A-20A of FIG. 19A.

A plurality of side openings 348 are formed in the wall of the distal end 342. Preferably, the side openings 348 are longitudinally and helically spaced along the distal end 342. The side openings 348 allow for fluid flow through the second lumen 341 in the event that the distal tip 344 clogs due to clotting, or gets sucked against the wall of the vessel into which the catheter assembly 300 is inserted. Preferably, the side openings 348 are generally circular, although those skilled in the art will recognize that the openings 348 may be oval, or other shape as well. Optionally, a most proximal side opening 349, along the flattened "D" side, may be oval, as shown in FIG. 19, in order to accommodate a guide wire to pass therethrough in a guide wire weave technique that will be explained in greater detail later herein.

Referring to FIG. 14, a proximal end 350 of the second catheter 340 has a cross-section that changes from the "D-shape" to a generally circular shape. Also, the cross-section of the second lumen 341 changes from the "D-shape" to a circular shape. The proximal end 350 of the second catheter 340 ends in a second extension tube 352 that is molded to the proximal end 350 of the second catheter 340. The second extension tube 352 is preferably constructed from a thermoplastic urethane elastomer, such as PELLETHANE® polyurethane, or some other suitable material. A second clamp 353 is disposed over the second extension tube 352. Preferably, the second clamp 353 is a Roberts clamp, or another suitable clamp known to those skilled in the art.

A proximal end 354 of the second extension tube 352 includes the luer fitting 326, which is preferably identical to the luer fitting 326 on the first extension tube 322. Alternatively, the luer fitting 426 (FIGS. 18 and 18a) may be releasably connected to the proximal end 354 of the second extension tube 352.

A catheter ingrowth cuff 360 is applied by the user to the exterior of the catheter assembly 300 along the portion of the catheter assembly 300 that includes the first and second catheters 310, 340, respectively, being non-releasably bonded to each other. The cuff 360 is preferably constructed from a synthetic woven material such as polyester, although those skilled in the art will recognize that other suitable materials may be used. An interior side 362 of the cuff 360 preferably includes an adhesive backing that allows the inserting physician to install the cuff 360 along the length of the catheter assembly 300 in a location as determined by the inserting physician. After the desired location for attaching the cuff 360 is located, the cuff 360 is wrapped around the exterior of the catheter assembly. As shown in FIG. 14, the cuff 360 is disposed along the exterior of the first and second lumens 310, 340, respectively, where the first and second lumens 310, 340 are bonded together.

The catheter assembly 300 preferably, would also include the hub 150 that is described above with respect to FIGS. 1, 15 and 16, with the hub 150 being releasably connected to the catheter assembly 300.

The catheter assembly 300 can be inserted into the patient in one of several insertion methods. For the catheter assembly 300 with the luer fittings 326 fixedly connected to each of the first and second extension tubes 322, 352, respectively, or if the luer fittings 426 are used, the catheter assembly 300 may be inserted into a blood vessel for a short term, without the need for the subcutaneous tunnel 16, or long term, where the subcutaneous tunnel 16 (FIGS. 11 and 12) is preferred.

For long term use with the subcutaneous tunnel 16, if the luer fittings 326 are used on the catheter assembly 300, the catheter assembly must first be tunneled prior to inserting the catheter assembly 300 into the vessel being catheterized. However, if the luer fittings 426 are used, the catheter assembly 300 may first be inserted into the vein to be catheterized, and the proximal end of the catheter assembly 300, without the luer fittings 426, may then be retrograde tunneled through the tunnel 16. After the catheter assembly 300 has been tunneled, the luer fittings 426 are connected to the extension tubes 322, 352.

Regarding the insertion of the catheter assembly 300 into the vessel to be catheterized, the incision 18 is made as described above with respect to the catheter assembly 100 (FIGS. 1 to 10). The guide wire (not shown) is inserted into the internal jugular vein 22 as described above. The distal ends 312, 342 of the catheters 310, 340 may be split apart from each other by pulling apart the bond 180 between the catheters 310, 340. The distal ends 312, 342 may be split a distance as preferred by the particular inserting physician.

One method of inserting the catheter assembly 300 into the vessel by using a guide wire is to use a guide wire weave technique. In this technique, the proximal end of the guide wire is inserted into the distal tip opening 346 in the distal tip 344 of the second catheter 340. The guide wire is advanced and drawn out of the second catheter 340 through the oval side opening 349. The guide wire is then advanced into the distal tip opening 316 in the distal tip 314 of the first catheter 310, and advanced through the first lumen 311 and exits the proximal end 324 of the first extension tube 322. The catheter assembly 300 is then advanced into the internal jugular vein 22 a desired distance. When the catheter assembly 300 is inserted the desired distance, the guide wire is removed by pulling the guide wire proximally from the catheter assembly 300. Optionally, the hub 150 may be connected to the catheter assembly 300 as described above with respect to the catheter assembly 100. The hub 150 is sutured to the patient's skin to secure the catheter assembly 300 to the patient.

Alternatively, instead of using the guide wire weave technique as described above, a stylet may be inserted into the proximal end 354 of the second extension tube 352 and inserted distally through the first lumen 311 and out the distal tip 344. The proximal end of the guide wire is inserted into the distal end of the stylet and the stylet with the catheter assembly 300 is slid over the guide wire and into the internal jugular vein 22. After the catheter assembly 300 is inserted a desired distance, the guide wire and the stylet are removed from the catheter assembly 300. The hub 150 may be connected to the catheter assembly 300 as described above with respect to the catheter assembly 100. The hub 150 is sutured to the patient's skin to secure the catheter assembly 300 to the patient.

Alternatively, the dilator and tearable sheath as described above with respect to the catheter assembly 100 may be used to insert the catheter assembly 300 into the jugular vein 22.

An alternate embodiment of a catheter assembly 400 according to the present invention is shown in FIGS. 21-23. Preferably, the catheter assembly 400 is similar to the catheter disclosed in U.S. Pat. No. 5,947,953 to Ash et al. and U.S. Pat. No. 6,190,349, also to Ash et al. which are both incorporated herein in their entireties by reference. However, as shown in FIG. 22, while first and second catheters 410, 440 each have a generally "D-shaped" cross section, distal tips 412, 432 of the first and second catheter 410, 430, respectively, change to oval and circular cross sections, as seen in FIG. 23.

Additionally, a catheter retaining cuff 460 may be fixedly connected to the exterior of the catheters 410, 430. Alternatively, the catheter retaining cuff 460 may be selectively fixable to the exterior of the catheters 410, 430 along the length of the catheters 410, 430, preferably between a hub 450 and a split location where the distal ends 412, 432 of the first and second catheters 410, 430 are split from each other.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for inserting a multiple catheter assembly comprising steps of:
   making an incision near an area of a body to be catheterized; and
   inserting at least a portion of a multiple catheter assembly into the area of the body to be catheterized, the multiple catheter assembly comprising:
   a cannulating portion;
   a first catheter comprising a first proximal end region, a first lumen extending through the first catheter, and a first distal end region terminating in a first distal tip, at least a portion of the first catheter residing in the cannulating portion, the first catheter further comprising a first outer surface defining at least the first lumen extending through the first catheter, the first outer surface further defining a cross-section at the first distal tip and a cross-section in the cannulating portion, the first lumen defining a cross-section at the first distal tip and a cross-section in the cannulating portion, the first distal end region comprising a first transition region tapering the first outer surface from the cross-section defined by the first outer surface in the cannulating portion to the cross-section defined by the first outer surface at the first distal tip, the first transition region further tapering the first lumen from the cross-section defined by the first lumen in the cannulating portion to the cross-section defined by the first lumen at the first distal tip; and
   a second catheter comprising a second proximal end region, a second lumen extending through the second catheter, and a second distal end region terminating in a second distal tip, at least a portion of the second catheter residing in the cannulating portion, the second catheter further comprising a second outer surface defining at least the second lumen extending through the second catheter, the second outer surface further defining a cross-section at the second distal tip and a cross-section in the cannulating portion, the second lumen defining a cross-section at the second distal tip and a cross-section in the cannulating portion, the second distal end region comprising a second transition region tapering the second outer surface from the cross-section defined by the second outer surface in the cannulating portion to the cross-section defined by the second outer surface at the second distal tip, the second transition region further tapering the second lumen from the cross-section defined by the second lumen in the cannulating portion to the cross-section defined by the second lumen at the second distal tip, wherein the cross-section defined by the first outer surface at the first distal tip is different in shape from the cross-section defined by the second outer surface at the second distal tip, wherein the first lumen and the second lumen are independent from each other for facilitating simultaneous flow in opposite directions, and wherein at least a portion of the first and second outer surfaces of the first and second catheters are releasably joined by a splittable bond for allowing the first and second catheters to be at least partially longitudinally split from each other.

2. The method according to claim 1, further comprising a step of at least partially separating the first proximal end region of the first catheter from the second proximal end region of the second catheter.

3. The method according to claim 1, further comprising a step of attaching a tunneling device to the first and second proximal end regions of the first and second catheters.

4. The method according to claim 3, further comprising a step of subcutaneously tunneling the first and second proximal end regions of the first and second catheters.

5. The method according to claim 4, further comprising a step of removing the tunneling device from the first and second proximal end regions of the first and second catheters.

6. The method according to claim 3, wherein the first and second proximal end regions of the first and second catheters are at least partially separated.

7. The method according to claim 1, further comprising a step of releasably attaching a hub to the first and second proximal end regions of the first and second catheters.

8. The method according to claim 7, wherein a distal end of the hub is adapted to maintain the first and second catheters against each other in the cannulating portion of the multiple catheter assembly and a proximal end of the hub is adapted to separate a proximal end of the first catheter from a proximal end of the second catheter, the method further comprising steps of:

placing the first and second catheters together into the distal end of the hub;

at least partially separating the first proximal end region of the first catheter from the second proximal end region of the second catheter; and placing the first and second proximal end regions of the first and second catheters into the hub, whereby the hub separates the proximal end of the first catheter from the proximal end of the second catheter.

9. The method according to claim 7, further comprising a step of longitudinally translating the hub along the first and second proximal end regions of the first and second catheters to a desired location along the first and second proximal end regions of the first and second catheters.

10. The method according to claim 7, further comprising a step of releasably connecting the hub to the body.

11. The method according to claim 1, further comprising steps of releasably connecting a first extension tube to a proximal end of the first catheter and releasably connecting a second extension tube to a proximal end of the second catheter.

12. The method according to claim 1, further comprising a step of at least partially separating the first and second catheters from each other, wherein the step of inserting comprises inserting the first and second distal tips of the first and second catheters in juxtaposed relation to each other through the incision and into the area of the body to be catheterized.

13. The method according to claim 12, further comprising a step of closing the incision after the first and second distal tips are inserted in the area to be catheterized.

14. The method according to claim 12, further comprising a step of, prior to inserting the first and second distal tips, inserting a stylet into at least one of the first and second lumens.

15. The method according to claim 12, further comprising a step of, prior to inserting the first and second distal tips, inserting a guide wire through the incision and into the area of the body to be catheterized.

16. The method according to claim 15, wherein the second catheter comprises at least one side opening located in the second outer surface between the first distal tip of the first catheter and the second distal tip of the second catheter, and wherein the method further comprises a step of inserting a proximal end of the guide wire into the second distal tip, out of one of the at least one side opening, into the first distal tip, through the first lumen, and out a proximal end of the second catheter.

17. The method according to claim 12, further comprising a step of, prior to inserting the portion of the multiple catheter assembly, tunneling the first and second distal tips of the first and second catheters through a subcutaneous tunnel.

18. The method according to claim 12, further comprising a step of, after inserting the first and second distal tips of the first and second catheters into the area of the body to be catheterized, tunneling first proximal end of the first catheter and a second proximal end of the second catheter through a subcutaneous tunnel.

19. The method according to claim 18, further comprising a step of, after tunneling the first and second proximal ends of the first and second catheters, connecting a luer connector to each of the proximal ends of the first and second catheters.

* * * * *